(12) United States Patent
Hummer

(10) Patent No.: US 12,352,737 B2
(45) Date of Patent: Jul. 8, 2025

(54) SYSTEM AND METHOD FOR MEASURING CHEMICALS, ANALYTES AND OTHER FACTORS IN FOOD

(71) Applicant: Matthew Hummer, Atlantic Beach, FL (US)

(72) Inventor: Matthew Hummer, Atlantic Beach, FL (US)

( * ) Notice: Subject to any disclaimer, the term of this patent is extended or adjusted under 35 U.S.C. 154(b) by 171 days.

(21) Appl. No.: 17/025,132

(22) Filed: Sep. 18, 2020

(65) Prior Publication Data

US 2021/0088496 A1    Mar. 25, 2021

Related U.S. Application Data

(60) Provisional application No. 62/902,413, filed on Sep. 19, 2019.

(51) Int. Cl.
*G01N 33/12* (2006.01)
*G01D 21/02* (2006.01)

(52) U.S. Cl.
CPC ............ *G01N 33/12* (2013.01); *G01D 21/02* (2013.01)

(58) Field of Classification Search
CPC .............. G01N 33/12; G01N 33/02; G01N 2033/0096; G01N 33/025; G01N 33/04; G01N 33/10; G01N 2035/00207; G01N 33/523; G01N 33/526; G01N 2496/80; G01N 1/00; G01N 1/02; G01N 29/226; G01N 1/4044; G01N 1/28; G01N 1/40; G01N 27/3273; G01N 33/66; G01N 33/5438; G01N 2035/00277; G01N 27/28; G01N 27/3271; G01N 27/3272; G01D 21/02; G01D 9/007; A61B 2562/0295; A61B 5/14532; A61B 5/14865; A61B 2560/0443; A61B 5/6833; A61B 2562/227; A61B 5/14546; A61B 5/1473; A61B 5/6849; A61B 5/14503; A61B 2562/12; A61B 5/0031; A61B 5/6801;

(Continued)

(56) References Cited

U.S. PATENT DOCUMENTS 4,980,294 A * 12/1990 Elias ...................... G01N 33/12
436/21
5,024,816 A * 6/1991 Arai ....................... G01N 33/12
422/68.1

(Continued)

OTHER PUBLICATIONS

Dincer, C., Bruch, R., Costa-Rama, E., Fernandez-Abedul, M., Merkoci, A., Manz, A., Urban, G., & Guder, F. (Mar. 15, 2019). Disposable Sensors in Diagnostics, Food, and Environmental Monitoring. Wiley Online Library. (Year: 2019).*

(Continued)

*Primary Examiner* — Daniel R Miller
*Assistant Examiner* — Eric Sebastian Von Wald
(74) *Attorney, Agent, or Firm* — Lippes Mathias LLP

(57) ABSTRACT

A system and method for measuring chemicals, analytes or other factors in food. The present invention relates to invasive transcutaneous measurement and minimally-invasive or non-invasive transdermal measurement of chemicals and analytes related to spoilage and contamination in a consumable host, primarily seafood and meat as well as other perishable foods. The invention also measures and monitors other factors including temperature, humidity, pH, moisture and location.

14 Claims, 14 Drawing Sheets

(58) Field of Classification Search
CPC .......... A61B 5/6843; A61B 2560/0468; A61B 2562/16; A61B 2560/0412; A61B 17/3468; A61B 2017/0023; A61B 5/0004; A23V 2002/00; A23B 5/055; A23B 7/055; A23L 3/375; A23L 5/00; A23L 17/00; A61M 2205/12; A61M 5/14276; A61M 5/20; A61M 2205/50; A61M 2205/582; A61M 2205/8206; A61M 2230/201; A61M 5/178; B65G 2201/0202; B26B 29/063; Y10S 435/973; Y10S 426/00; Y10S 250/91; Y02A 40/90; G01K 2207/02; G01K 2207/08; G05B 2219/36453; G05B 2219/37095; G05B 2219/36451; G06K 19/0703; H01H 71/0228; H05K 5/0256; H04N 1/32614; B01L 3/0275; B01L 3/0279; B01L 3/00; B01L 3/0289; B01L 2200/025; B01L 2200/026; B01L 2200/028; B01L 2200/04; B01L 2300/044; B01L 2300/0627; B01L 2300/0645; B01L 2400/0683

See application file for complete search history.

(56) References Cited

U.S. PATENT DOCUMENTS

| | | | | |
|---|---|---|---|---|
| 10,278,732 | B2 * | 5/2019 | Schoonmaker | A61B 5/14503 |
| 10,989,724 | B1 * | 4/2021 | Holmes | G01N 35/02 |
| 11,237,161 | B2 * | 2/2022 | Khattak | B01L 3/5029 |
| 2010/0198142 | A1 * | 8/2010 | Sloan | G16H 20/10 |
| | | | | 345/173 |
| 2010/0237850 | A1 * | 9/2010 | Salem Al-Ghamdi | |
| | | | | G01N 33/12 |
| | | | | 324/72 |
| 2010/0331657 | A1 * | 12/2010 | Mensinger | A61B 5/0022 |
| | | | | 340/870.07 |
| 2011/0021889 | A1 * | 1/2011 | Hoss | A61B 5/7221 |
| | | | | 600/310 |
| 2011/0077490 | A1 * | 3/2011 | Simpson | A61B 5/6848 |
| | | | | 600/345 |
| 2012/0149245 | A1 * | 6/2012 | Ralston | A61B 5/150022 |
| | | | | 439/660 |
| 2014/0114155 | A1 * | 4/2014 | Hutchinson | A61B 5/150549 |
| | | | | 600/347 |
| 2014/0227796 | A1 * | 8/2014 | Gold | B01L 3/5029 |
| | | | | 422/69 |
| 2017/0030853 | A1 * | 2/2017 | Hodges, Jr. | G06K 7/10366 |
| 2017/0248622 | A1 * | 8/2017 | Khattak | H04M 1/72403 |
| 2018/0231496 | A1 * | 8/2018 | Brennan | G01N 27/4163 |
| 2021/0132022 | A1 * | 5/2021 | Stead | G01N 33/74 |

OTHER PUBLICATIONS

Patel, P. D. (2002). (Bio)sensors for measurement of analytes implicated in food safety: a review. TrAC Trends in Analytical Chemistry, 21(2), 96-115. (Year: 2002).*

Mello, L., & Kubota, L. (2002). Review of the use of biosensors as analytical tools in the food and drink industries. Food Chemistry, 77(2), 237-256. (Year: 2002).*

* cited by examiner

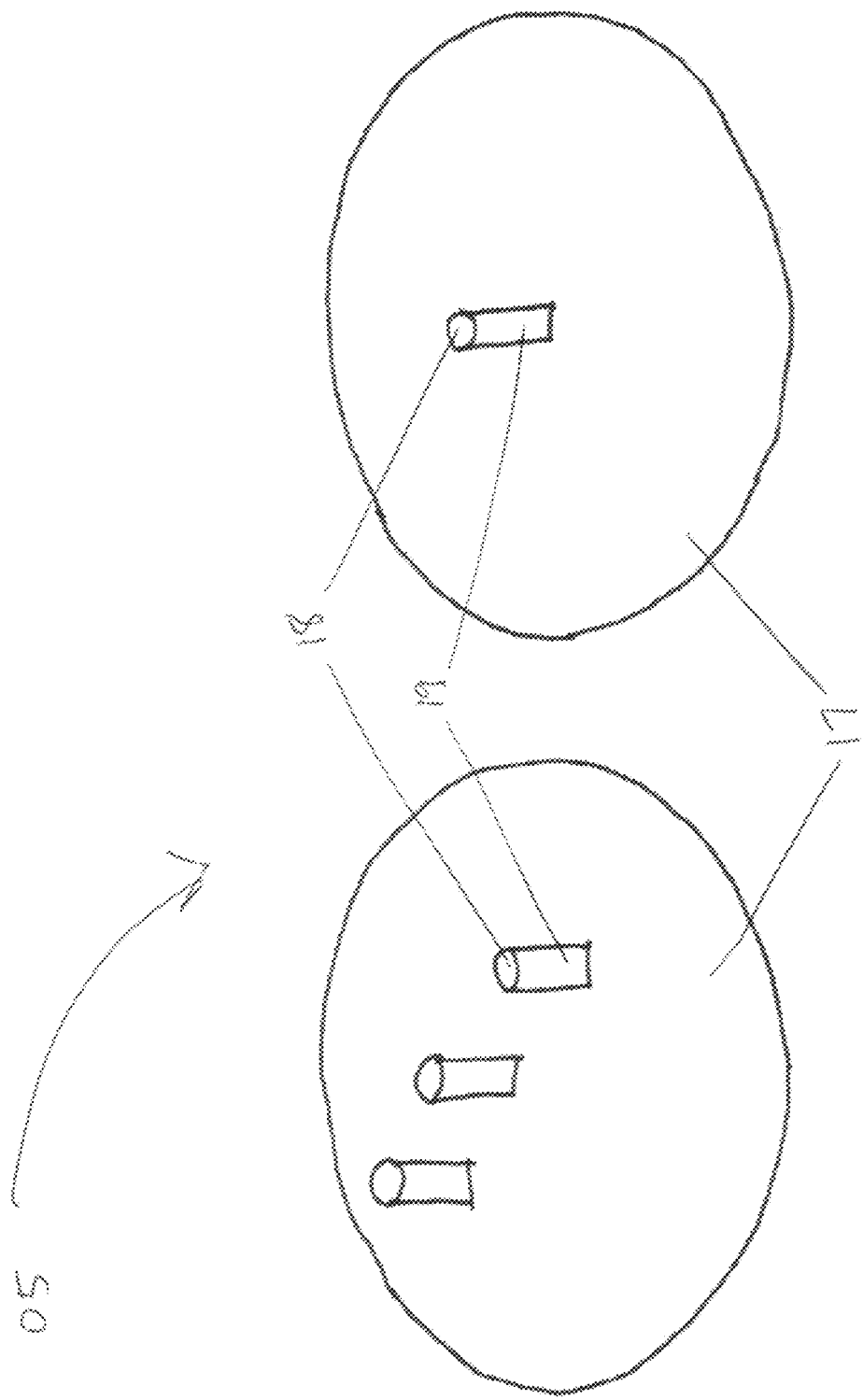

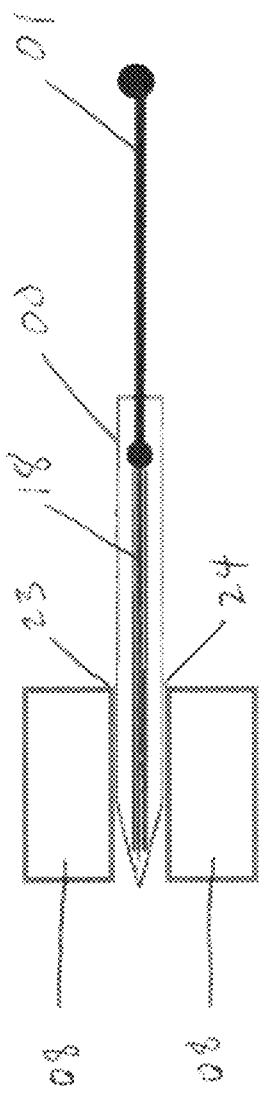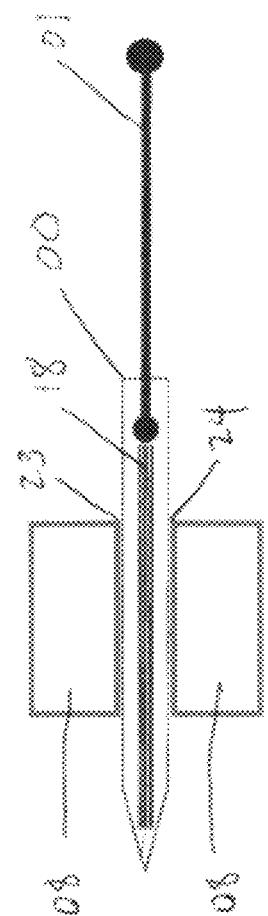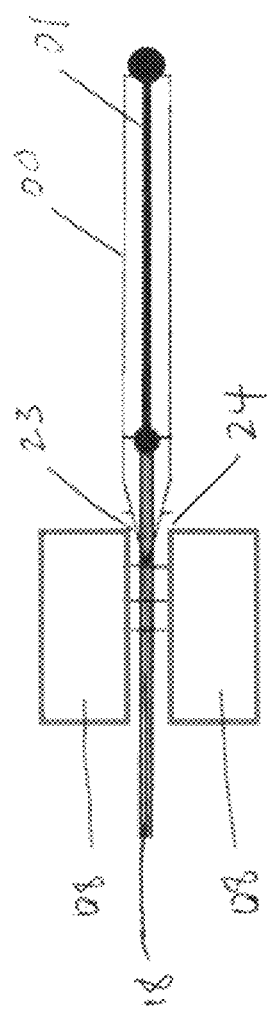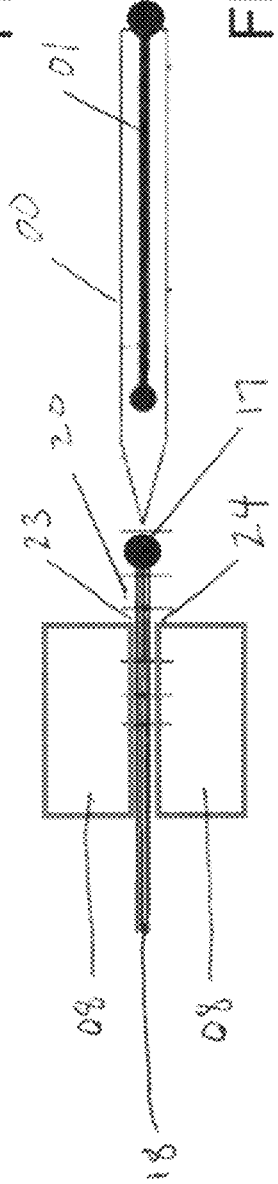
FIG. 10A
FIG. 10B
FIG. 10C
FIG. 10D

SYSTEM AND METHOD FOR MEASURING CHEMICALS, ANALYTES AND OTHER FACTORS IN FOOD

CROSS REFERENCE TO RELATED PATENTS AND APPLICATIONS

This application claims priority to and the benefit of the filing date of U.S. Provisional Patent Application Ser. No. 62/902,413, filed Sep. 19, 2019, which application is hereby incorporated by reference.

FIELD

The present exemplary embodiment relates to systems and methods for measuring or monitoring chemicals, analytes and other factors in food.

BACKGROUND

The Food and Drug Administration (FDA) requires shippers, carriers, loaders and receivers of food to follow certain rules, regulations and requirements for transporting perishables. The rules and regulations are enforced by the Food Safety Modernization Act (FSMA) signed into law on Jan. 4, 2011. Specifically, the final rule on the sanitary transportation of human and animal food (STF) establishes requirements for vehicles and transportation equipment, transportation operations, training for food handlers and transportation operators, written procedures and record-keeping among other enforcement mechanisms for ensuring temperature control is maintained throughout the supply chain.

Section 111 of STF specifically requires documentation to ensure proper temperatures are maintained for the duration of food transport within the United States. The rule sets the following responsibilities: 1) shippers must provide a complete report to the receiver of goods upon request that validates proper temperature conditions in staging areas prior to shipment 2) carriers must provide evidence of appropriate temperature monitoring before, during and time of delivery 3) consistent temperature monitoring and reporting is required by shippers and carriers throughout all stages of transportation in the cold chain. The STF is one of seven foundational rules proposed since January 2013 to create a modern, risk-based framework for food safety in the U.S. The goal of these rules are to prevent practices during transportation that create food safety risks, such as failure to properly refrigerate food, inadequate cleaning of vehicles between loads, and failure to properly protect food.

Food spoilage and contamination is a significant problem. Each year, over 53 million people in the U.S. become sick from food, with over 128,000 hospitalizations and over 3,000 deaths as a result from foodborne illness. Foodborne illnesses are estimated to cost the U.S. economy more than $55.5 billion a year. The estimate accounts for costs associated with food stores, restaurants, hotels and other food service organizations. The costs include medical treatment, lost productivity and foodborne illness-related mortality, but does not include the high cost of a damaged reputation to a business, which could add several million dollars per outbreak to the total estimated cost of foodborne illness.

Such high costs to public and private entities provide ample justification for investing in food safety. Among such investments include making food safety part of company culture, adopting the latest technologies, digitizing data gathering and record keeping and taking steps to reduce human error and even automating processes and procedures for testing food and transmitting the results to the appropriate decision makers.

SUMMARY

Methods, systems and devices are disclosed for addressing the significant challenges of food safety through applications for measuring and monitoring of chemicals in food. Specifically, methods and devices for real-time measurement of chemical concentrations and other environmental factors such as temperature, moisture, humidity and pH affecting the quality, safety and security of food, as well as tracking location, are disclosed.

It will be appreciated that throughout this disclosure the terms detection, measuring, and monitoring are interchangeably used and are intended to have the same meaning, which is to provide the level of data and information necessary for the user of the system. It will also be appreciated that the system detects the absence or presence or concentration levels of chemicals, compounds, elements, molecules, mixtures, analytes, biomaterial, microorganisms, bacteria, virus, pathogens, contaminants, toxins and other factors such as pH, temperature, sugar content, nutrient availability, humidity, moisture and location. The device can also be used to measure concentrations of biological material associated with metabolic engineering through systems of biology of industrial microorganisms and DNA sequencing, synthesis and editing. All these factors are herein referred to throughout this disclosure as "concentrations of chemicals" or simply "chemicals" or "analytes".

It should be further appreciated that chemicals associated with total volatile basic nitrogen (TVB-N) are of particular interest in one application. These chemicals include, but are not limited to, ammonia, trimethylamine (TMA), dimethylamine (DMA) and hypoxanthine (XOD). TVB-N is the amount of basic nitrogen-containing chemicals distilled from an alkalized extract or suspension of a fishery product. The bases, amines, in the distillate are determined by titration with standard acid. The amines all have one basic nitrogen atom in the molecule and TVB is expressed on a nitrogen basis, typically mg nitrogen/100 g of sample. The main component of TVB from very fresh fish is ammonia and, as fish spoils, increasing amounts of trimethylamine (TMA) are present. Small amounts of dimethylamine (DMA) are often present in TVB from spoiled fish.

This one application can be used to supplement, compliment or displace current methods for measuring TVB-N. Current methods include sampling a protein-free extract of fish muscle and preparing with 0.6 N perchloric acid. An aliquot of the extract is taken, alkalinized with sodium hydroxide. The volatile nitrogenous bases are distilled and trapped in boric acid. The concentration of the bases is determined by titration with standard acid.

Current methods of TVB-N sample preparation involve taking a fish sample of at least 100 g (preferably a total fillet) and homogenize thoroughly by cutting. From frozen fish, e.g. fillet blocks, cut a 100-200 g sample of approx. 2 cm thickness, place it in a water-tight plastic bag and thaw, e.g. by immersing the bag in a gently stirred water bath at about 20° C. but not more than 25° C.; thaw time: approx. 15 min. Bigger skin and bone pieces should be removed prior to homogenization. Weigh 10.0 g from the well-homogenized fish flesh sample into the mixing vessel. Add 90.0 mL perchloric acid solution, blend for two minutes with a high-speed mixer and then filter through a filter paper. The extract thereby obtained can be kept for at least seven days at a temperature between approximately 2° C. and 6° C.

TVB-N concentration expressed in mg/100 g sample is calculated with the following equation:

$$TVBN = \frac{(Vs - Vb) * 0.14 * 2 * 100}{m}$$

Throughout this disclosure the terms sensor and monitor and detector are used interchangeably. It will be appreciated that the present disclosure is not limited to any particular sensor type of design. However, the monitor/detector or array of detectors can include but are not limited to: electrochemical, chemiresistor, electronic tongue, electronic nose, or other type that measures electrical resistance or leverages a carbon particle, nano-particle, doped nano-tube, nano-tube, single walled nanotube, multi-walled nanotube, nanowire or other nano-type designs including nanoporous carbon, nanofilm, nanocages, nanochains, nanocomposites, nanofabrics, nanofibers, nanoflakes, nanoflower, nanomesh, polymers, conductive polymers, polyaniline, polypyrrole, graphene or other carbon form of the nanoscale. In some examples, molecularly imprinted polymer (MIPS), micro-electrochemical systems (MEMS) and/or Nanoelectromechanical systems (NEMS) can be used. In some examples, quantum dots or graphene quantum dots can be used. In still other examples, electrochemical, electrochemical amperometric, metal oxide, metal oxide semiconductor, infrared sensor (nondispersive), thermal sensor (pellitor), photoionization (PID), graphene, hybrid and nanostructures, Quartz Microbalance, and/or field-effect transistor (FET) type devices can be used.

One example of a specific electrochemical design includes single-electrode and three-electrode sensors that include a working electrode (WE), reference electrode (RE) and a Counter Electrode (CE). The electrodes can be covered with a hydrogel, ionic gel or coating. In some cases, the coverings can double as a biofluid sampling platform and as a storage reservoir for electrochemical sensing; however, a hydrogel does not have to be used. The working electrodes could be composed of precision printed Prussian Blue (PB) transducer, the enzyme bioreceptor (GOx for glucose and AOx for alcohol).

Aspects of the present disclosure can include a sensor that measures and monitors the reduction of the hydrogen peroxide of the enzymatic reaction of the PB transducer. A biocatalytic reaction can include the following: 1) glucose+oxygen=(GOx)=hydrogen peroxide+gluconic acid 2) alcohol+oxygen=(AOx)=hydrogen peroxide+acetaldehyde.

Another type of sensor, also previously disclosed in U.S. Pat. No. 8,629,770, is a three-electrode design with working electrode, counter electrode and reference electrode and could have either an ionic liquid layer or a gel ionic liquid electrolyte film; however the gel does not have to be used especially for detection in fluids. The sensor is capable of detecting chemicals in various forms including air, liquid and through contact.

Specifically, the ionic liquid also known as hydrogel can be made of 1-butyl-3-methylimidazolium hexafluorophosphate. Other formulas can be of agarose/gelatin. This liquid as well as other liquids have desirable properties for such a use, including stability at high temperature, the ability to withstand moisture or humidity effects as well as high levels of ionic conductivity under ambient or extreme temperatures. Other similar ionic liquids may also be used in the sensor application. U.S. Pat. No. 8,629,770 discloses various other ionic liquids that serve as binder and electrolyte.

In accordance with a first aspect, a method for inserting a sensor into a host using an applicator is provided, the method comprising the steps of: providing an applicator for inserting a sensor into a host, wherein the sensor comprises at least one electrode formed from a conductive material; and a membrane disposed on an electroactive portion of the electrode, wherein the membrane is configured to control an influx of the analyte therethrough, wherein the at least one electrode is configured to a flexible connector assembly; placing a mounting unit on the host, wherein the mounting unit comprises of the flexible connector assembly and a housing/mounting unit for a removable/replaceable unit. The housing/mounting unit also could have a connector component that mates with a releasable connector component of the applicator unit.

In an exemplary embodiment, the step of inserting a sensor into a host comprises using the applicator to attach or to embed the sensor into the host. Additional support for attaching or embedding the sensor can be provided by at least one of barb or similar method suitable for keeping the sensor securely embedded in host. It should be appreciated that various methods and techniques can be used for inserting the sensor into the host securely. Furthermore, the sensor itself can be of needle or barb form, allowing the sensor to securely embed itself into the host. The barb may be of such design to not only improve sensor performance, but also the sensor's ability to remain applied or embedded in the host.

The sensor can comprise three electrodes, including a counter electrode (CE), a working electrode (WE) and a reference electrode (RE). All three electrodes can run through a material that separates two portions of the sensor, with the first portion being that of a portion embedded in the host and the second portion being that of a portion extending to the mounting unit, wherein a connector assembly can be used to join at least one of the sensor electrodes to the components of removable/replaceable unit, which selectively attaches to the mounting unit.

The sensor can be configured for continuous measurement of at least one analyte or chemical (e.g., glucose, lactate, xanthine, diamine, trimethylamine, histamine among others related to spoilage and contamination in a host).

The sensor can be inserted in the host by the applicator at a specific angle, wherein the angle is the best angle for the performance of the sensor.

The membrane can further comprise an enzyme domain.

The membrane can further comprise an electrode domain.

The membrane can further comprise an interference domain.

The membrane can be at least partially formed by a coating process.

The membrane can substantially resist ascorbate flux therethrough.

In an exemplary embodiment, the connector assembly comprises a surface with printed elements or components such as electrodes (RE, WE and CE) extending from three pin placements whereby the three sensor electrodes (RE, WE and CE) join. The electrodes are held in place using silver-loaded epoxy or like substance. The connector assembly unit joins the sensor electrodes of the sensor to the electrical components contained in the removable/replaceable unit that selectively attaches to the housing/mounting unit/connector component.

The removable/replaceable unit that selectively attaches to the housing/mounting unit/connector component; the removeable/replaceable unit comprises a measurement/analyzer, processor, memory, communication circuitry and an active/passive power source operatively coupled to the sensor, processor, memory and the communication circuitry for supplying power thereto, and wherein the communication circuitry is configured to transmit data to an associated receiver.

In accordance with a second aspect, a method for calibrating the sensor is provided. The method comprises the steps of taking measurements of concentrations of chemicals or analytes over intervals of various time periods; accounting for various factors including temperature, humidity, moisture, pressure among other factors that affect sensor functionality; using algorithms to develop the most accurate measurements possible and transmitting data to an associated receiver.

In an exemplary embodiment, the intervals of various time periods comprise 30 seconds, 60 seconds, 90 seconds, 120 seconds, 150 seconds, 180 seconds among other intervals wherein the length of the interval is directly correlated with the amount of data collected.

An algorithm can be used to account for deviations of sensor sensitivity from the average or median sensor measurement, wherein such deviations are less than about 25 percent; wherein such deviations are less than about 20 percent; wherein such deviations are less than about 15 percent; wherein such deviations are less than about 10 percent; wherein such deviations are less than about 5 percent, wherein such deviations are less than about 2 percent and wherein such deviations are less than about 1 percent and wherein such deviations are less than about 0.5 percent.

Factors such as temperature, humidity, pH and length of time in storage or transport and journey mapping can be components of algorithms used to correct for measurement deviations from the median measurement value.

A line of best fit, least square method among other estimation methods can be used to calibrate sensor and produce the most accurate readings.

Calibration data, calculations, algorithms and calibration identifications are stored in the memory of the removable/replaceable unit that can be part of the housing/mounting unit/connector component or made to selectively attach to the housing/mounting unit/connector component.

In accordance with a third aspect, a method for programming or calibrating the sensor is provided. The method comprises the steps of establishing a baseline measurement of chemical concentration; estimating a rate of increase in chemical concentration over consecutive days of cold storage or cold transport; using the calculated rate of spoilage increase and baseline estimate to establish threshold levels of spoilage wherein alerts can be sent to associated receiver when thresholds are breeched or not breeched; establishing decision-based thresholds that correlate to actions such as "safe to consume" or "not safe to consume" among other action-based alerts that prompt remedial action. Related remedial action could include: re-routing a shipment, canceling a shipment, combining a shipment with another shipment, inspecting the cold storage equipment, replacing the cold storage equipment, reimbursing a supplier or business partners or adjusting sales price of food items among other actions that relate to supplying and selling perishable food.

The baseline measurement of chemical concentration can be deemed the line of best fit according to disclosers in the second embodiment.

Consecutive days of cold storage or transport can be any number of days or less than one day or less than one hour or less than 30 minutes.

Cold storage or transport conditions can be any temperature, but typically range between 0 and 10 degrees Celsius.

In accordance with a fourth aspect, a method of defining when data shall be transmitted to an associated receiver and how the associated receiver can learn from transmitted and non-transmitted data is provided. The method comprises the steps of establishing criteria for data transmission; programming software to follow the established criteria; programming software to link disparate data points; programming software to learn from linking disparate data points; incorporating learning into decision criteria and algorithms in the third aspect.

Learning from transmitted and non-transmitted data can comprise gathering and analyzing data of chemical concentration as well as conditions that can have a causal link to such chemical concentrations such as temperature, pH, humidity, moisture among other factors.

Establishing criteria for data transmission can comprise setting thresholds associated with decisions or actions intended to optimize supply chain resources, mitigate spoilage and contamination.

Programming software to follow established criteria, can include setting commands whereby conditions of data related to chemical concentrations and associated environment and conditions can be or cannot be satisfied.

Programming software to link disparate data points can include setting commands for acquiring information and linking disparate data points and setting rules, reasoning to reach approximate or definite conclusions, wherein such methods include the ability to take self-correcting steps.

Incorporating learning into decision criteria and algorithms can further comprise testing the validity of learning algorithms.

In accordance with a fifth aspect, a method of monitoring levels of chemicals and other conditions associated with spoilage and contamination in shipments of food is provided. The method comprises the steps of: deploying at least one of a monitoring device configured to produce and transmit data in response the absence or presence of at least one chemical or factor associated with spoilage and contamination; activating the monitoring device, enabling data transmission capability; periodically retrieving data produced by the monitoring device; using such data to populate decision-grade analytics; relying on such decision-grade analytics to optimize scarce supply chain resources; rely on such decision-grade analytics to adjust sale price and product orders so that product sales are maximized and food waste is minimized and rely on such decision-grade analytics to mitigate the high cost of food spoilage and contamination.

The monitoring device comprises at least one of detector/sensor component joined to a removable/replaceable unit comprising of a processor, memory, communication circuitry and a power source operatively coupled to the detector/sensor, processor, memory and the communication circuitry for supplying power thereto, and wherein the communication circuitry is configured to transmit data to an associated receiver. The monitoring device can also further comprise of a measurement/analyzer.

Data transmission capabilities can be activated individually or in a batch process.

Data retrieval process can be set according to custom requirements suitable to supplying the necessary level of data and information for business decision making.

The process of using decision-grade analytics for business decision making can be semi-automated, fully automated or linked to a distributed control system for inventory management tasks such as order placement, transport routing, transport re-routing, transport transloading, stocking products, picking products from inventory that are deemed unsuitable for sale and adjusting sale price of products.

BRIEF DESCRIPTION OF THE DRAWINGS

FIG. 6A is a perspective view of an exemplary sensor that can be embedded in a host or attached to a host;

FIG. 6B is a perspective view of an exemplary sensor that can be embedded in a host or attached to a host;

FIG. 10A is a schematic illustration of the injection mechanism/device/component and the removeable/replaceable injection needle assembly in a first position;

FIG. 10B is a schematic illustration of the injection mechanism/device/component and the removeable/replaceable injection needle assembly in a second position;

FIG. 10C is a schematic illustration of the injection mechanism/device/component and the removeable/replaceable injection needle assembly in a third position;

FIG. 10D is a schematic illustration of the injection mechanism/device/component and the removeable/replaceable injection needle assembly in a fourth position;

DETAILED DESCRIPTION

Figure 1:
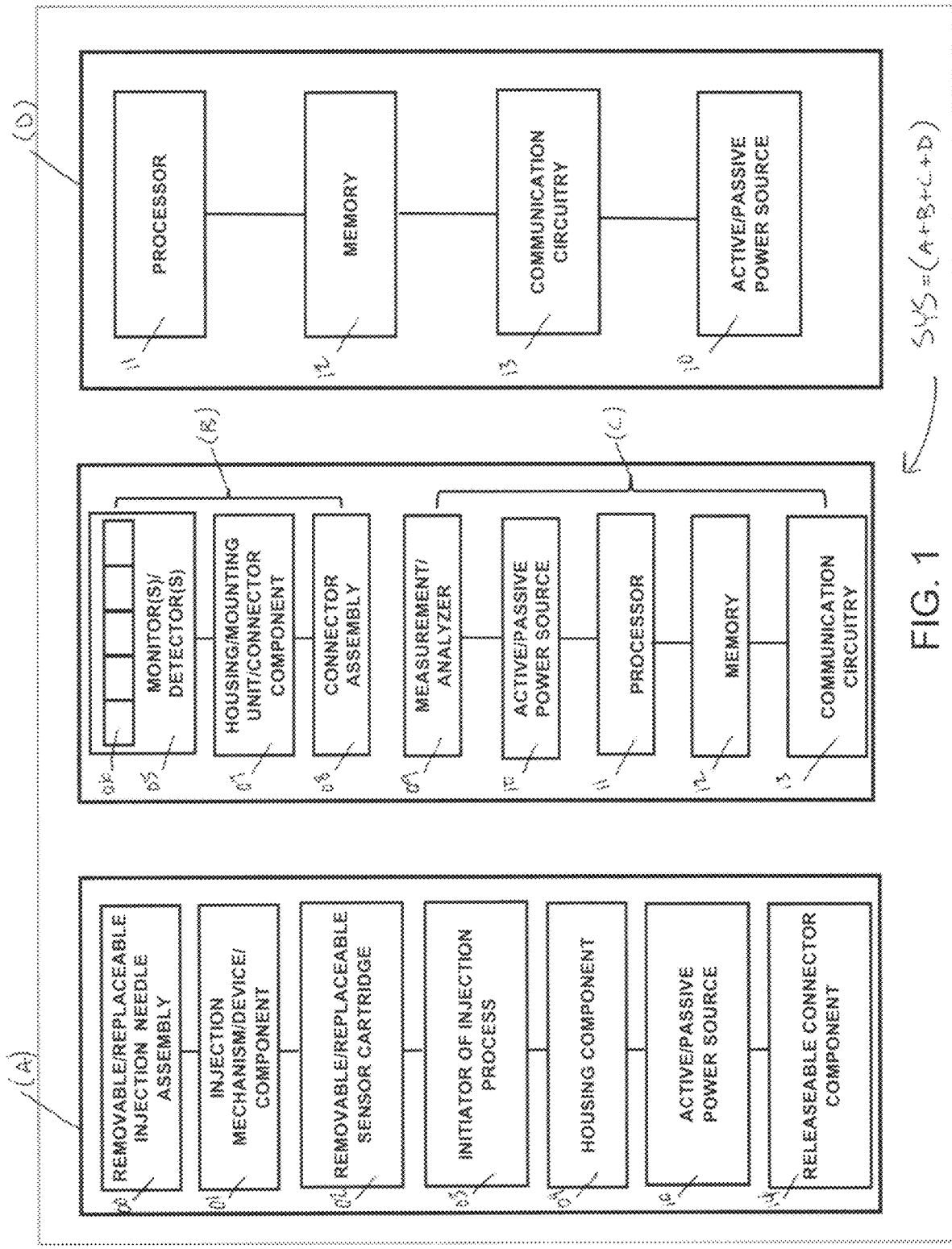
FIG. 1 illustrates a general schematic diagram of an exemplary system for measuring chemical concentrations and other factors in food in accordance with the present disclosure.

The following description and examples illustrate some exemplary embodiments of the present disclosure in detail. Those of skill in the art will recognize that there are numerous variations and modifications of this invention that are encompassed by its scope. Accordingly, the description of a certain exemplary embodiment should not be deemed to limit the scope of the present disclosure.

Definitions

In order to facilitate an understanding of the preferred embodiments, a number of terms are defined below.

The term "analyte" as used herein is a broad term and is used in its ordinary sense, including, without limitation, to refer to a substance or chemical constituent in a biological fluid (for example, blood, interstitial fluid, cerebral spinal fluid, lymph fluid or urine) that can be analyzed. Analytes can include naturally occurring substances, artificial substances, metabolites, and/or reaction products. In some embodiments, the analyte for measurement by the sensing regions, devices, and methods are glucose, hypoxanthine, diamine, histamine, trimethylamine among others associated with spoilage, contamination and pathogens. However, other analytes are contemplated as well, including but not limited to acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, glucose-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, Plasmodium vivax, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; glucose-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxy-progesterone; hypoxanthine phosphoribosyl transferase; immunoreactive trypsin; lactate; lead; lipoproteins ((a), B/A-1, β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, Dracunculus medinensis, Echinococcus granulosus, Entamoeba histolytica, enterovirus, Giardia duodenalisa, Helicobacter pylori, hepatitis B virus, herpes virus, HIV-1, IgE (atopic disease), influenza virus, Leishmania donovani, leptospira, measles/mumps/rubella, Mycobacterium leprae, Mycoplasma pneumoniae, Myoglobin, Onchocerca volvulus, parainfluenza virus, Plasmodium falciparum, poliovirus, Pseudomonas aeruginosa, respiratory syncytial virus, rickettsia (scrub typhus), Schistosoma mansoni, Toxoplasma gondii, Trepenoma pallidium, Trypanosoma cruzi/rangeli, vesicular stomatis virus, Wuchereria bancrofti, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins and hormones naturally occurring in blood or interstitial fluids can also constitute analytes in certain embodiments. The analyte can be naturally present in the biological fluid, for example, a metabolic product, a hormone, an antigen, an antibody, and the like. Alternatively, the analyte can be introduced into the body, for example, a contrast agent for imaging, a radioisotope, a chemical agent, a fluorocarbon-based synthetic blood, or a drug or pharmaceutical composition, including but not limited to insulin; ethanol; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbiturates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-dihydroxyphenylacetic acid (DOPAC), homovanillic acid (HVA), 5-hydroxytryptamine (5HT), and 5-hydroxyindoleacetic acid (FHIAA).

The term "host" as used herein is a broad term and is used in its ordinary sense, including, without limitation, to refer to seafood and meat such as fish, mammals, birds and other categories of vertebrates and non-vertebrates.

The phrase "continuous (or continual) analyte sensing" as used herein is a broad term and is used in its ordinary sense, including, without limitation, to refer to the period in which monitoring of analyte concentration is continuously, continually, and or intermittently (regularly or irregularly) performed, for example, about every 3 to 20 minutes.

The term "electrochemically reactive surface" as used herein is a broad term and is used in its ordinary sense, including, without limitation, to refer to the surface of an electrode where an electrochemical reaction takes place. For example, a working electrode measures hydrogen peroxide produced by the enzyme-catalyzed reaction of the analyte detected, which reacts to create an electric current. Glucose analyte can be detected utilizing glucose oxidase, which produces H2O2 as a byproduct. H2O2 reacts with the surface of the working electrode, producing two protons (2H+), two electrons (2e−) and one molecule of oxygen (O2), which produces the electronic current being detected.

The term "electronic connection" as used herein is a broad term and is used in its ordinary sense, including, without limitation, to refer to any electronic connection known to those in the art that can be utilized to interface the sensing region electrodes with the electronic circuitry of a device, such as mechanical (for example, pin and socket) or soldered electronic connections.

The term "interferant" and "interferants," as used herein, are broad terms and are used in their ordinary sense, including, without limitation, to refer to species that interfere with the measurement of an analyte of interest in a sensor to produce a signal that does not accurately represent the analyte measurement. In one example of an electrochemical sensor, interferants are compounds with oxidation potentials that overlap with the analyte to be measured.

The terms "operable coupled" and "operably connected" and "operably linked" as used herein are broad terms and are used in their ordinary sense, including, without limitation, to refer to one or more components linked to one or more other components. The terms can refer to a mechanical connection, an electrical connection, or a connection that allows transmission of signals between the components. For example, one or more electrodes can be used to detect the amount of analyte in a sample and to convert that information into a signal; the signal can then be transmitted to a circuit. In such an example, the electrode is "operably linked" to the electronic circuitry.

The term "baseline" as used herein is a broad term and is used in its ordinary sense, including, without limitation, is the component of an analyte sensor signal that is not related to the analyte concentration. In one example of a hypoxanthine sensor, the baseline is composed substantially of signal contribution due to factors other than hypoxanthine (for example, interfering species, non-reaction-related hydrogen peroxide, or other electroactive species with an oxidation potential that overlaps with hydrogen peroxide). In some embodiments wherein a calibration is defined by solving for the equation y=mx+b, the value of b represents the baseline of the signal.

The term "algorithm," as used herein, is a broad term and is used in its ordinary sense, without limitation, to refer to a computational process (for example, programs) involved in transforming information from one state to another, for example, by using computer processing.

The term "regression," as used herein, is a broad term and is used in its ordinary sense, including, without limitation, to refer to finding a line for which a set of data has a minimal measurement (for example, deviation) from that line. Regression can be linear, non-linear, first order, second order, or the like. One example of regression is least squares regression.

The term "calibration," as used herein, is a broad term and is used in its ordinary sense, including, without limitation, to refer to the process of determining the relationship between the sensor data and the corresponding reference data, which can be used to convert sensor data into meaningful values substantially equivalent to the reference data. In some embodiments, namely, in continuous analyte sensors, calibration can be updated or recalibrated over time as changes in the relationship between the sensor data and reference data occur, for example, due to changes in sensitivity, baseline, transport, metabolism, or the like.

The terms "interferants" and "interfering species," as used herein, are broad terms and are used in their ordinary sense, including, without limitation, to refer to effects and/or species that interfere with the measurement of an analyte of interest in a sensor to produce a signal that does not accurately represent the analyte concentration. In one example of an electrochemical sensor, interfering species are compounds with an oxidation potential that overlap that of the analyte to be measured, thereby producing a false positive signal.

Turning to the FIGURES, FIG. 1 illustrates a general configuration of an exemplary system for measuring chemical concentrations, analytes and other factors in food (SYS). The system (SYS) can include four separate major components each having their own sub-components. Some systems can include three separate major components. This is the case when the monitor/detector component (B) and the removeable/replaceable unit (C) are built as a single unit.

The first major component is of various applicator designs for embedding a sensor in a host or attaching a sensor to a host (A). The second major component is the monitor/detector component (B) that has a housing/mounting unit/connector component that joins through a connector assembly (08) to the third major component, a removeable/replaceable unit (C). The connector assembly (08) can be also designed to be part of the monitor/detector component (B) or it can be part of the removeable/replaceable unit (C). The removable/replaceable unit (C) contains a transmitter among other components that communicate with the fourth major component, an associated receiver (D). All together the four major components (A+B+C+D) make-up the system for measuring chemicals, analytes and other factors is food (SYS).

The first major component, the applicator for embedding a sensor in a host or attaching a sensor to surface of host (A), can have various configurations. However, FIG. 1 presents a general configuration consisting of at least one of a removeable/replaceable injection needle assembly (00) or mechanism/device/component for injecting or embedding a sensor in a host (01). Other features of the applicator (A) can include: a removeable/replaceable cartridge (02) containing at least one of sensor; an initiator of the process for injecting or embedding the sensor in a host (03); a housing component (04) and releasable connector component (14) that joins the applicator (A) with the housing/mounting unit/connector component (07) of the monitor/detector (B).

The releasable connector component (14) is releasable upon successful deployment of a transcutaneous sensor in a host or a transdermal sensor in a host. The releasable connector (14) helps guide the sensor for proper embedding in a host or attaching to a host. Specifically, the releasable connector (14) allows the sensor to be embedded or attached at the proper angle, depth among other factors that allow the sensor to be properly joined to the housing/mounting unit (07) of the monitor/detector (B) through the connector assembly (08).

Figure 2:
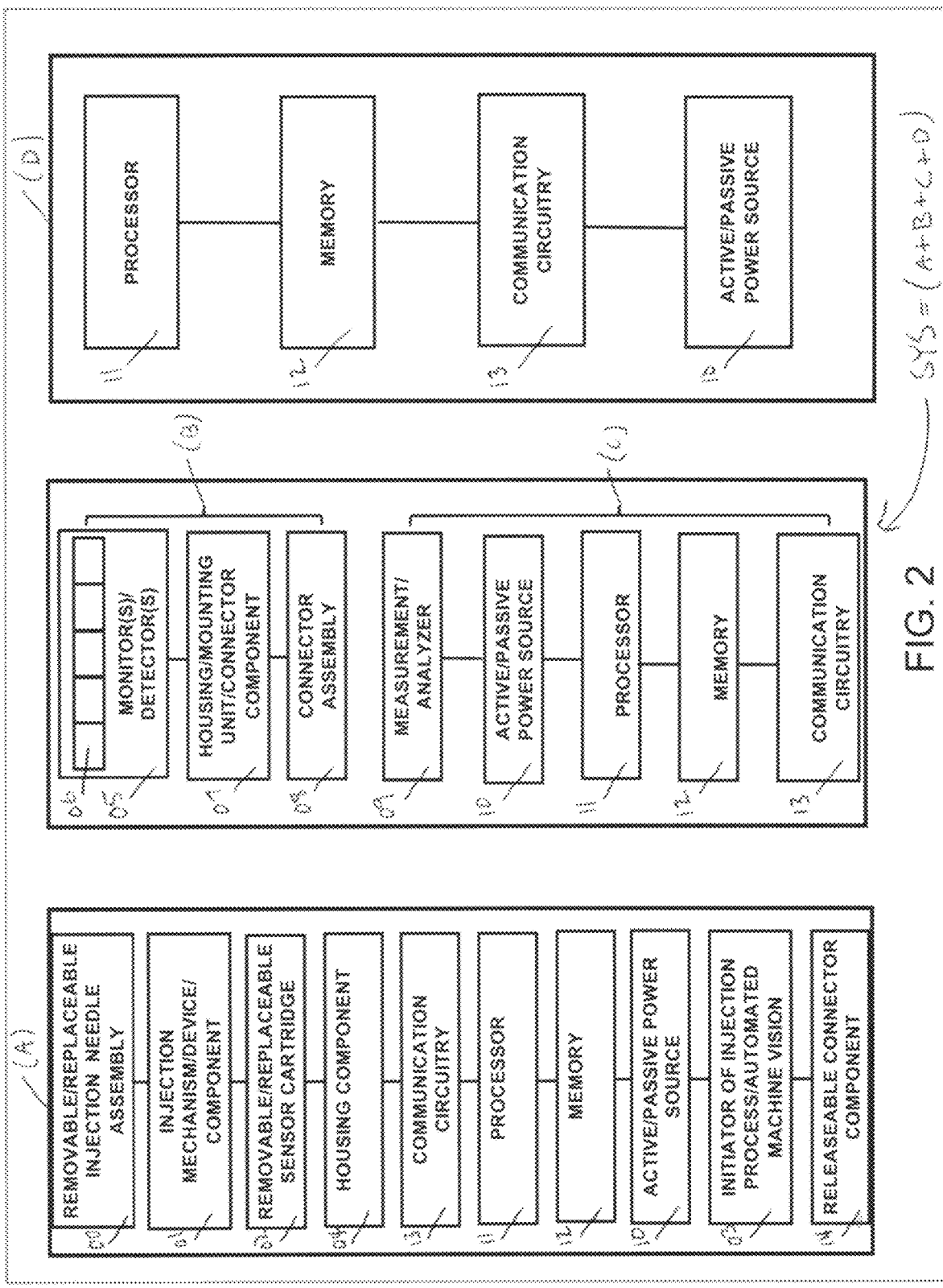
FIG. 2 illustrates another general schematic diagram of an exemplary system for measuring chemical concentrations and other factors in food in accordance with the present disclosure.

One sub-component of the sensor applicator (A) is a removeable/replaceable injection needle assembly (00) further referenced in FIG. 2. Although the embodiments described herein suggest manual insertion and/or retraction of the various components, automation of one or more of the stages can also be employed. For example, spring-loaded mechanisms that can be triggered to automatically insert and/or retract the monitor/detector, needle assembly, or other cooperative applicator components can be implemented as part of the applicator (A).

Another sub-component of the sensor applicator (A) is an injection mechanism/device/component (01) that can include various sub-components including an accompanying mechanism used to release the removeable/replaceable injection needle (00), a mechanism for providing pressure or force required to embed a sensor in a host as well as a device for reloading injection mechanism with another sensor from the removeable/replaceable sensor cartridge (02).

It can be appreciated that the injection mechanism/device/component (01) involve various features to embed sensor in a host or attach sensor to a host. Among these features include a component such as a barb or like device to hold the sensor in place once successfully embedded in a host.

Another sub-component of the applicator (A) is a removeable/replaceable sensor cartridge (02). Among the disclosed sensor cartridge designs includes a circular cartridge that revolves away from an empty chamber towards a chamber with a sensor that is loaded into the injection mechanism (01), specifically the interior of the removeable/replaceable injection needle assembly (00), to be embedded in a host. Another disclosed cartridge design includes a rectangle cartridge with a spring mechanism that pushes the sensor into the injection mechanism (01), specifically the interior of the removeable/replaceable injection needle assembly (00), to be embedded in host. Yet another cartridge design uses the force of gravity to push the sensor into the injection mechanism, specifically the interior of the removeable/replaceable injection needle assembly (00), to be embedded in host. Still another design utilizes both a spring mechanism and the force of gravity to push the sensor into the injection mechanism.

Another sub-component of the sensor applicator (A) is an initiator of the injection process (03). Such initiator can be in the form of a button, switch, trigger, key, turnkey, tab or dial among other components that initiate the process of injecting, attaching or adhering. The initiator can also be automatically initiated based on various factors including time, motion, light among other conditions that could signal for the sensor injection process to be initiated. The initiator of the injection process (03) is connected to the injection mechanism/device/component (01).

Another sub-component of the sensor applicator (A) is a housing (04). Such housing encloses the devices and components of the applicator (A) in a way that protects them and allows the applicator (A) to function optimally. Certain features of the housing also allow the applicator to connect to other system components or to be handled properly for successful injection of the sensor. The housing can include various portions of a hand-held or stationary device. In the case of a hand-held-device, the housing can include a handle, body portion, clips, cartridges among other types of ordinary or inordinacy housing components. In the case of a stationary device, the housing can include protective covers, clips and even areas where electrical cords enter the applicator (A).

Another sub-component of the sensor applicator (A) is an active/passive power source (10). Such sources of power can include a photovoltaic cell, solar cell, antenna or other type of power source including any form wired transmission.

Another sub-component of the sensor applicator (A) is a releasable connector component (14). The connector component (14) mates with a connector component of the housing/mounting unit (07) of the monitor/detector (B) to ensure that the transcutaneous sensor is embedded properly in a host. In addition to ensuring the monitor/detector (05) is properly attached or embedded in a to host, the releasable connector component (14) enables precise coupling between the monitor/detector (05) and the connector assembly (08), which joins the monitor/detector (B) and the removeable/replaceable unit (C).

It should be appreciated that various designs of the applicator (A) do not necessarily have to include a releasable connector component (14) or an active/passive power source (10). For example, in situations where the sensor can be embedded in a host properly without requiring the releasable connector (14) or an injection mechanism/device/component coupled to an active passive power source (10).

The second major component of the monitor/detector (B) is also shown in FIG. 1. The monitor/detector (B) can comprise a plurality of sensors (06) of various types for detecting chemicals, analytes and other factors such as temperature, pH level, nutrient availability, moisture, humidity among others. The monitor/detector (05) can be connected to a housing/mounting unit/connector component (07) that joins to a removeable/replaceable unit (C), which is the third major component of the system (SYS) through a connector assembly (08).

Among the types of detector/monitor of the present disclosure is an electrochemical cell that provides an output signal by which the presence or absence of an analyte, such as glucose, hypoxanthine, diamine, histamine, trimethylamine among others associated with spoilage, contamination and pathogens. For example, in an electrochemical cell, an analyte (or a species derived from it) that is electro-active generates a detectable signal at an electrode, and this signal can be used to detect or measure the presence and/or amount within a biological sample and can be in accordance with similar methods set forth in U.S. Pat. No. 8,629,770. In some conventional sensors, an enzyme is provided that reacts with the analyte to be measured, and the byproduct of the reaction is qualified or quantified at the electrode. An enzyme has the advantage that it can be very specific to an analyte and also, when the analyte itself is not sufficiently electro-active, can be used to interact with the analyte to generate another species which is electro-active and to which the sensor can produce a desired output. In one conventional amperometric xanthine oxidase-based hypoxanthine sensor, immobilized xanthine oxidase catalyses the oxidation of xanthine to form hydrogen peroxide, which is then quantified by amperometric measurement (for example, change in electrical current) through a polarized electrode.

According to an exemplary embodiment of the present disclosure, a monitor/detector (05) or plurality of sensors (06) can be embedded in a host or applied to the surface of the host. The monitor/detector (05) can be deployed by itself or it can be attached to the housing/mounting unit/connector component (07) through the connector assembly (08) and deployed as a monitor/detector (B). When the monitor/detector (05) is deployed by itself, care must be taken that the monitor/detector (05) is properly embedded in the host. Care must also be taken that the monitor/detector (05) is properly joined with the housing/mounting unit/connector component (07) through the connector assembly (08) so that the monitor/detector (B) can be properly joined to the removeable/replaceable unit (C).

Typically, the housing/monitoring unit/connector component (07) is adhered to the host first, followed by the deployment of the monitor/detector (05) using the applicator (A); a process further described in FIGS. 11A-11D. However, in some cases the monitor/detector (05) can be embedded in the host or attached to a host using the applicator (A) first, followed by attaching the housing/monitoring unit/connector component (07) to the monitor/detector (05) by way of the connector assembly (08).

For example, the housing/mounting unit/connector component (07) can first be adhered to the host using any such method of adhesive, pin, clip, band or tag. Then the monitor/detector (05) can be deployed through holes of the connector assembly (08) attached to the housing/mounting unit/connector component (07) (see FIGS. 10A-11D). Then the monitor/detector (B) is joined with the removeable/replaceable unit (C) through the connector assembly (08).

One of the disclosed applicator designs includes a releasable connector component (14) that temporarily joins with the housing/mounting unit/connector component (07) in order to guide the monitor/detector (05) as it is embedded or adhered to the host. The releasable connector (14) also ensures that the monitor/detector (05) is properly joined with the housing/mounting unit/connector component so that the monitor/detector (05) can be properly joined with components of the removable/replaceable unit (C), primarily the power source (10) and the measurement/analyzer (09).

The third major component of a removeable/replaceable unit (C) is joined to the monitor/detector (B) through the connector assembly (08). In one example, the removeable/replaceable unit (C) comprises the measurement/analyzer (09) and an active/passive power source (10). The measurement/analyzer (09) is connected to the monitor/detector (05) by way of the connector assembly (08) and is used to control electrical current or measure resonance frequency or produce other types of sensor data. The measurement/analyzer can be one of a potentiostat, amperostat, glavanostat, ammeter, multimeter, ohmmeter, rheoscope or voltmeter among other devices or components that control electrical current and measure resonance frequency or electrical current.

The active/passive power source (10) operatively coupled to the monitor(s)/detector(s) (05) and the measurement/analyzer (09), processor (11), memory (12), communication circuitry (13) for supplying power thereto, and the communication circuitry can be configured to transmit data in response to the detection of the absence or presence of at least one chemical by the detector component. Other components of the removeable/replaceable unit (C) can include: a processor (11) for processing the detector data; a memory (12) for storing and retrieving the detector data; communication circuitry (13) for transmitting data.

It should also be appreciated that the system for measuring chemicals, analytes and other factors (SYS) can also be designed without a removable/replaceable unit (C), in such a case the components of the removable/replaceable unit (C) and the components of the monitor/detector (B) would be combined into a single unit. Among various other beneficial features, the removable/replaceable unit (C) is intended for reuse across multiple chemical measurement systems (SYS). The process for reuse includes washing, sterilizing and refurbishing before reuse.

The fourth major component is an associated receiver (D) that receives transmitted data or information from the monitor/detector (B) and/or the removeable/replaceable unit (C). The receiver (D) of the illustrated exemplary embodiment includes a processor (11), memory (12), communication circuitry (13), and an active/passive power source (10). Such power sources can include: a battery, a photovoltaic cell, solar cell or an antenna for receiving electromagnetic energy. It will be appreciated that the associated receiver (D) can include a wide variety of additional components as is conventional. Such additional components can include a display device, input device, various sensors (such as those that track location, pressure, motion and temperature), various antennas and other peripheral devices.

It should also be appreciated that the system for measuring chemicals, analytes and other factors (SYS) can also have various applicator designs. Among the many possible designs are three specific designs for embedding a sensor in a host or applying a sensor to a host. One of such disclosed design is of a non-electric device; another disclosed design is of electric device and yet other disclosed designs are of electrical and automatic mechanisms and components. In some cases, the designs can leverage one or more of the designs (non-electric, electric or automatic). For example, a disclosed design has an active/passive power source as well as a component that automatically initiates the sensor injection process or a design could have an active/passive power source, but not always rely on the power source.

It should be appreciated that the various designs align to the various methods of harvesting, processing, packaging, transporting, storing and selling food, primarily seafood and meat. For example, the powerless design can be used in the field where power or electrical systems are not widely available. Furthermore, the mechanical, powerless design can be used to tag seafood immediately upon harvest or catch, establishing a digital record of the first point of tracking and tracing seafood or meat from farm to table. Whereas, the electrical and automated methods are more suitable to rapid processing and packaging performed in large scale.

FIG. 2 presents another exemplary arrangement of components for an automated applicator (A) as part of a system for measuring chemicals, analytes and other factors (SYS). Such designs leverage electrical and automated methods and applicator designs. They also can include additional components that enable automatic deployment of sensor such as an initiator of the injection process that is automated by machine vision (15) or computer vision. Such components can require communication circuitry (13), a processor (11) and memory (12) among other related components.

It can be appreciated that sub-components of the other major components, monitor/detector (B), removeable/replaceable unit (C) and associated receiver (C) can have various changes as a result of the automated applicator (A).

The general purpose of the applicator (A) is to deploy a transcutaneous or transdermal monitor/detector in a host for measurement of chemicals or analytes related to spoilage or contamination. In one embodiment, an applicator (A) is provided for inserting the monitor/detector (05) through the host's skin at the appropriate insertion angle with the aid of an injection needle (00), and for subsequent removal of the needle using a continuous push-pull action. Preferably, the applicator comprises an applicator housing component (04) that can be in the form of a handle or body portion and guides the applicator components for embedding sensor in a host. The housing component (04) can also include an injection mechanism (01). The housing component (04) or more broadly the sensor applicator (A) can be configured to connect or mate with the mounting unit (07) during insertion of the sensor into the host through the releasable connector component (14). The mate between the applicator (A) and the mounting unit (07) can use any known mating configuration, for example, a snap-fit, a press-fit, an interference-fit, pressure fit or the like, to discourage separation during use. One or more release latches enable release of the releasable connector component (14), for example, when the connector component (14) is snap fit into the mounting unit housing/mounting unit (07) of the monitor/detector (B).

Figures 3A, 3B:
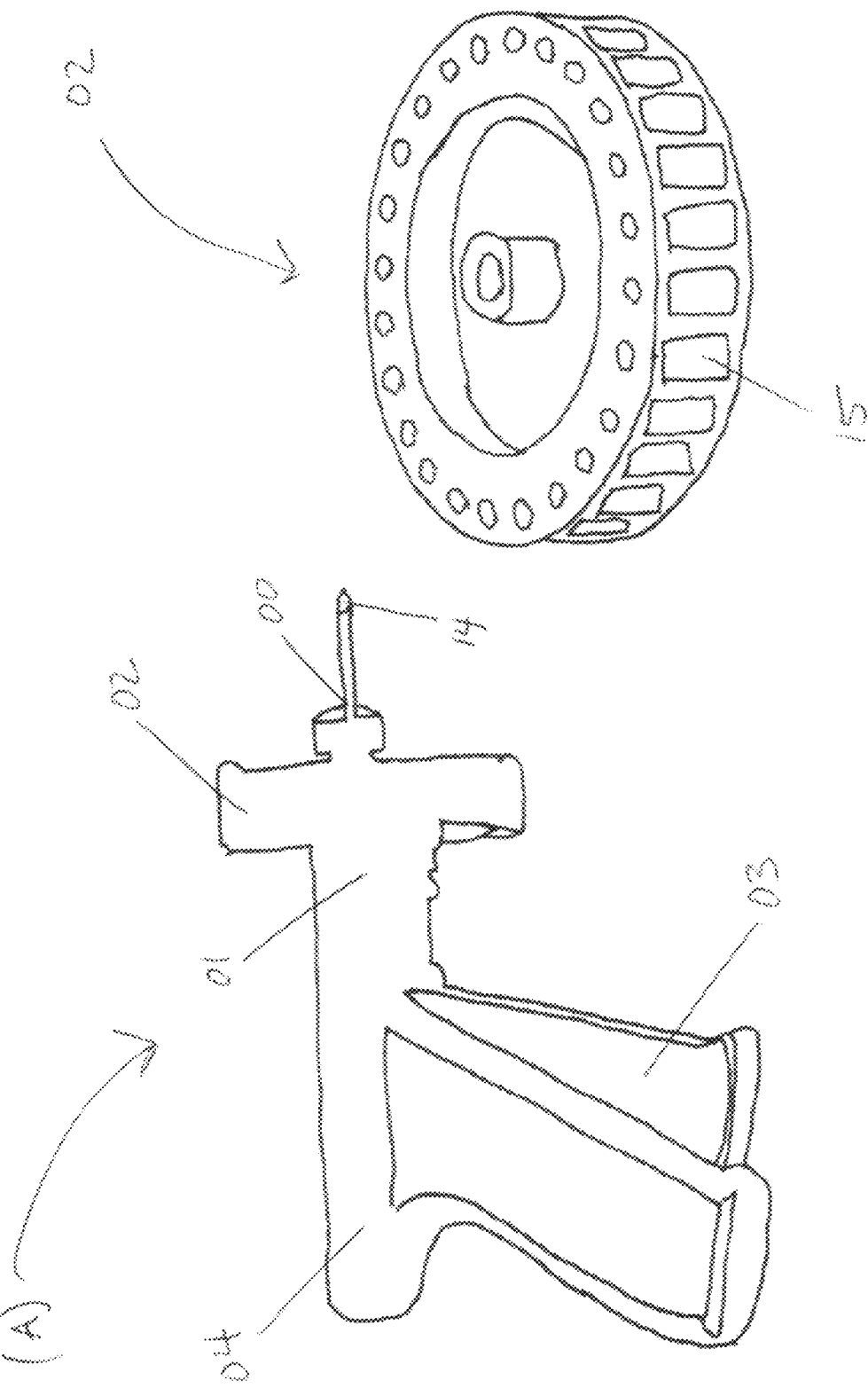
FIG. 3A is a side elevation view of an exemplary non-electric applicator device for embedding a sensor in a host along with an associated removeable/replaceable sensor cartridge in accordance with the present disclosure.
FIG. 3B is a perspective view of a removeable/replaceable sensor cartridge for use with the applicator of FIG. 3A.
Figure 4B:
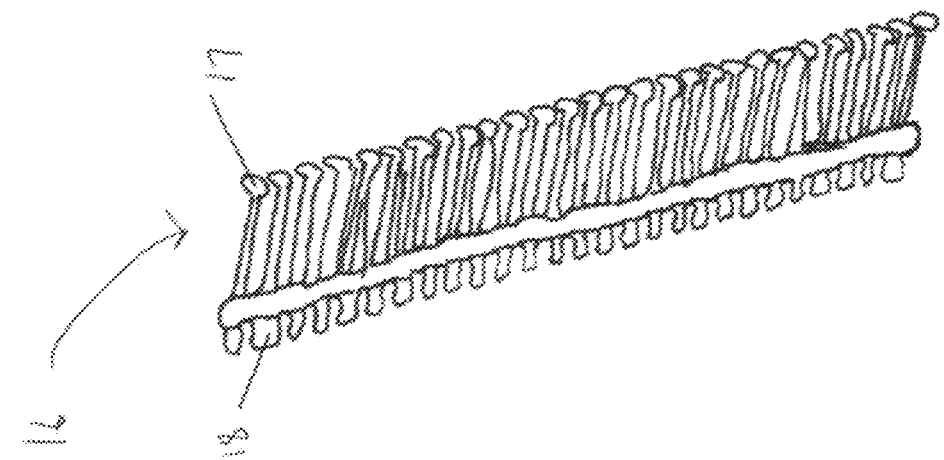
FIG. 4B is a perspective view of an exemplary clip device of sensors for use with the applicator of FIG. 4B.
Figure 4A:
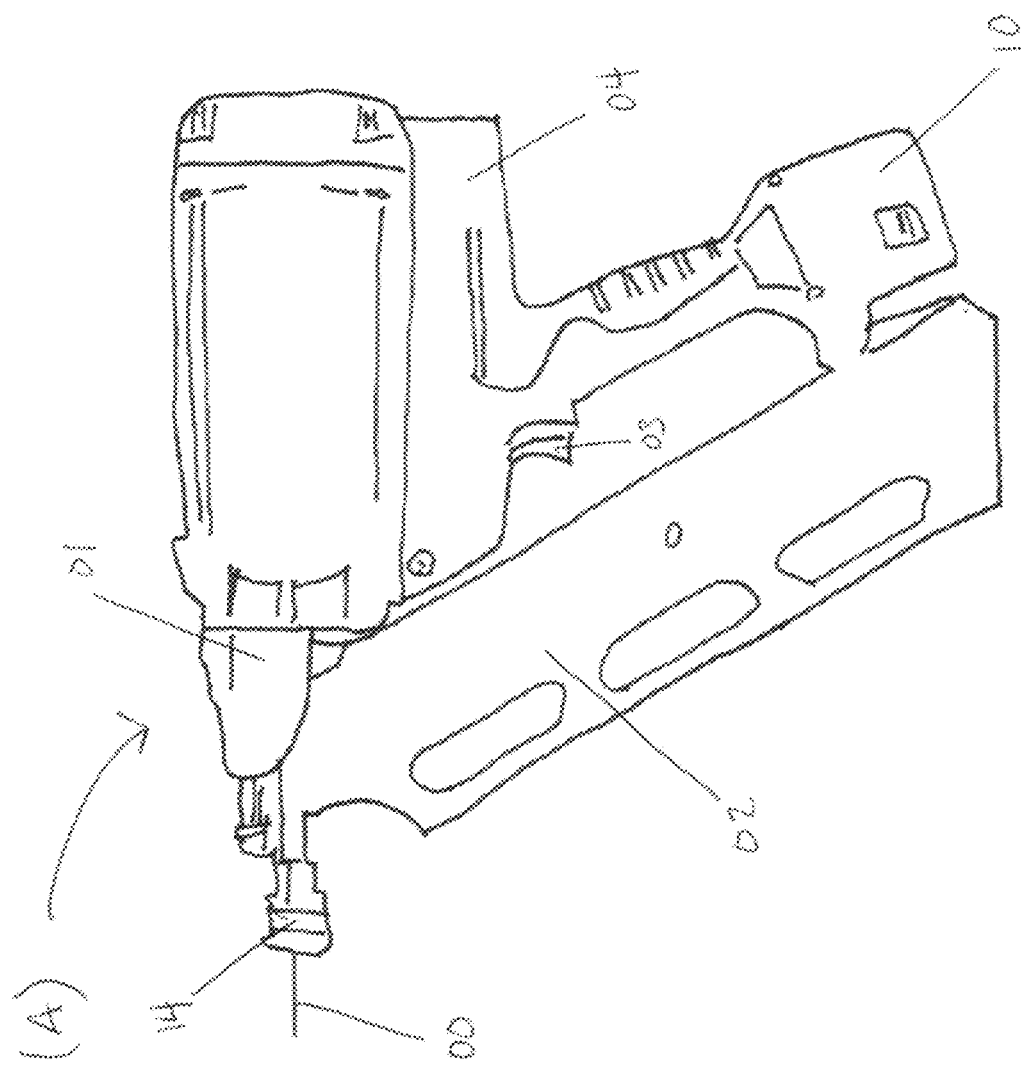
FIG. 4A is a side elevation view of an exemplary electric-powered applicator device for attaching or embedding a sensor in a host along with an exemplary associated clip of sensors in accordance with the present disclosure.
Figure 5:
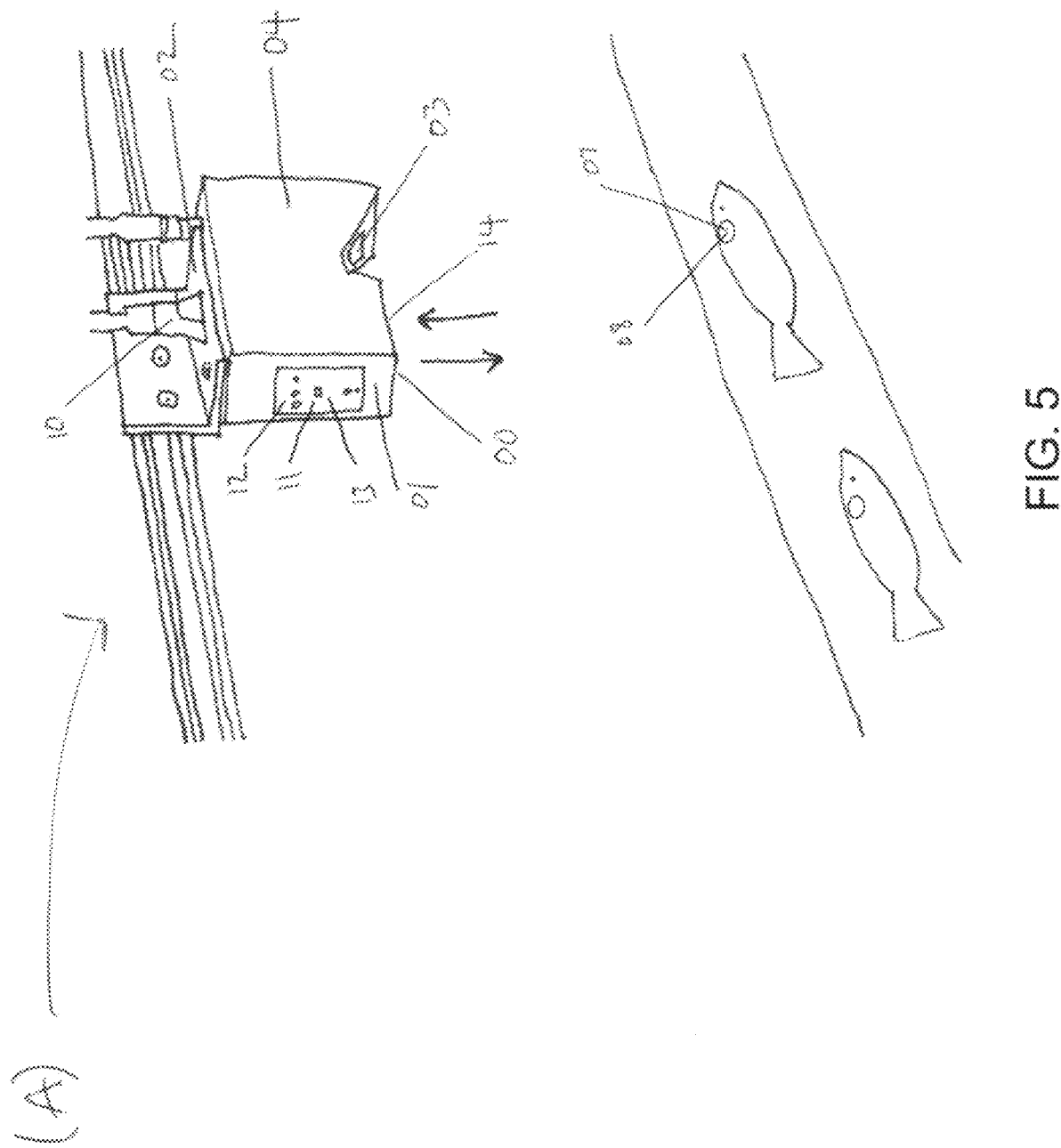
FIG. 5 is a perspective view of an exemplary automated applicator device for embedding or attaching a sensor in a host moving on a conveyor or like equipment in accordance with the present disclosure.

Turning to FIGS. 3-5, various exemplary sensor applicators are illustrated according to disclosures in FIGS. 1-2. FIG. 1 relates to FIGS. 3A-3B and 4A-4B and FIG. 2 relates to FIG. 5. In FIG. 3A, a non-electrical applicator (A) is shown and in FIG. 3B an accompanying removeable/replaceable sensor cartridge (02) is shown. The non-electrical applicator (A) relies on a mechanical injection mechanism/device/component (01) to push the monitor/detector (05) from inside of the removeable/replaceable injection needle assembly (00) through the connector assembly (08) of the monitor/detector component (B) to inside the host. The removeable/replaceable sensor cartridge (02) revolves in a circular motion as it is coupled to the injection mechanism/device/component (01). The coupled component moves the monitor/detector (05) from the chamber of the cartridge (15) to inside the chamber of the removeable/replaceable injection needle assembly (00) in place and ready for the injection process as illustrated in FIGS. 10A-10D.

The non-electrical applicator (A) includes a removeable/replaceable needle assembly (00), injection mechanism/device/component (01), removeable/replaceable sensor cartridge (02), initiator of the injection process (03) and a housing component (04). In some cases, the non-electrical applicator (A) can also include a releasable connector component (14) that mates with the housing/mounting unit/connector component (07), which is part of the monitor/detector component (B).

It will be appreciated that the exemplary sensor applicator (A) can be used to embed one or more monitors/detectors (06) in a host or one or more monitor/detector components (B). Typically, a single-electrode sensor or a three-electrode sensor is used to measure chemicals, analytes and other factors in a host. For embedding or attaching a three-electrode sensor, the same applicator can be used for all three electrodes or three different applicators can be used for the three different electrodes. When three different applicators are used, each applicator may be loaded with three different types of monitor/detector (05), specifically a working electrode (WE), counter electrode (CE) and a reference electrode (RE). A single applicator can also be designed to inject the three separate sensors (WE, CE and RE) using either a single remove/replaceable injection needle assembly (00) or multiple removeable/replaceable injection needle assemblies (00), one for each of the electrode types—WE, CE and RE. It can be appreciated that modifications to the applicator design can be made to accommodate a sensor with more than one electrode. Alternatively, a single-electrode monitor/detector (05) can be used, in which case a single removeable/replaceable injection assembly (00) is used.

FIG. 3B presents an exemplary removeable/replaceable sensor cartridge (02). The circular cartridge revolves enabling the chamber of the cartridge (15) to align with the injection mechanism (01) so that the sensor can be loaded inside the chamber removeable/replaceable injection needle assembly (00) and ultimately inserted into a host.

The illustration of FIG. 3B shows separate chambers (15) for each monitor/detector (05). Each chamber is similar in that it has a hole on one side allowing the monitor/detector (05) to exit the chamber of the sensor cartridge (15) to the injection mechanism (01) to be loaded inside of the removeable/replaceable injection needle (00) and ultimately embedded in a host. As previously disclosed the removeable/replaceable sensor cartridge (02) can be loaded with consecutive single-electrode sensors or the cartridge can be loaded with consecutive sets of three different electrode sensors (WE, CE and RE). Modifications such as color coding or similar methods can be used to ensure that the appropriate electrodes are embedded in the proper holes (23) of the connector assembly (08). Also, the circular removeable/replaceable sensor cartridge (02) can be disposable or single-use or it can be durable or multiple-use or re-use. In the case of multiple use, the sensors are assembled in a clip device, which stores individual sensors together as a single unit. The clip device can be inserted into the removeable/replaceable sensor cartridge (02) or inserted directly into the sensor applicator (A). It can also be the case that the sensors (05) can be manually or automatically deposited into the chamber of the sensor cartridge (15).

FIGS. 4A and 4B illustrate another exemplary applicator unit (A) and accompanying clip of monitor/detectors (16) that can be inserted into the removeable/replaceable sensor cartridge (02) or directly into the sensor applicator (A). The electrical applicator (A) in FIG. 4A relies on a power source (10) to drive the injection mechanism/device/component (01) in pushing the monitor/detector (05) from inside of the injection mechanism (01) through the removeable/replaceable injection needle assembly (00), passing through the connector assembly (08) of the monitor/detector component (B) to the inside the host. The exemplary removeable/replaceable sensor cartridge (02) is rectangular in shape and has a spring mechanism that pushes the monitor/detector (05) up from the sensor cartridge (02) in alignment with the injection mechanism (01). Once the sensor is aligned with the injection mechanism (01), it moves through the injection mechanism (01) through the removeable/replaceable needle assembly (00) and ultimately is embedded in the host as shown in FIGS. 10A-10D. The applicator also includes a housing component (04) in the form of a body portion and handle. The initiator of the injection process (03) of this exemplary applicator is in the form of a trigger. The exemplary applicator can also include a releasable connector component (14) that mates with the housing/mounting unit/connector component (07), which is part of the monitor/detector component (B).

FIG. 4B presents an exemplary clip device of sensors (16) that can go inside of the removeable/replaceable sensor cartridge (02) or can be attached directly to the sensor applicator (A). The illustration shows a vertical assembly of individual monitor/detectors (05) that can be placed inside of the removeable/replaceable sensor cartridge (02) shown in FIG. 4A. The monitors/detectors (05) in FIG. 4B move up through the sensor cartridge shown in FIG. 4A with the help of a spring mechanism in the cartridge and into the injection mechanism (01) and onto the needle assembly (00) to be embedded in a host. The clip device of sensors (16) can contain any number of monitors/detectors (05). The assembly of sensors can be of consecutive single-electrode sensors or consecutive sets of three-electrode sensors (WE, CE and RE). Similar to the other exemplary applicators, designs can be capable of embedding or attaching a single-electrode sensor or multiple electrode sensor simultaneously, consecutively or sequentially.

In general, the electric powered sensor applicator (A) and accompanying clip device of sensors (16) are designed for rapid deployment of monitor/detector (05). Such rapid deployment can be in the form of an assembly line or like food processing, packaging, storage and transportation processes. It can be appreciated that the sensor applicator (A) can have any number of type of modifications to its core component the injection mechanism/device/component (01).

With reference back to FIG. 2, FIG. 5 illustrates yet another exemplary applicator unit (A) that automatically deploys sensors. The applicator relies on a power source (10) to drive the injection mechanism/device/component (01) in pushing the monitor/detector (05) from inside of the injection mechanism (01) through the removeable/replaceable injection needle assembly (00), passing through the connector assembly (08), which can be attached to the housing/mounting unit/connector component (07) of the monitor/detector component (B) to the inside the host (as shown in FIGS. 10A-10D). The initiator of the injection process (03) is automated and powered by machine vision or like automatic, autonomous or computer-powered smart system.

With further reference to FIG. 2, the automatic, electrical powered sensor applicator includes: a removeable/replaceable injection needle assembly (00), injection mechanism/device/component (01), removeable/replaceable sensor cartridge (02), housing component (04), communication circuitry (13), processor (11), memory (12), active/passive power source (10) and an automated initiator of injection process (03) powered by machine vision or computer vision or like system. The applicator can also include a releasable connector component (14), but does not require one, especially if the sensor can be properly embedded in a host.

FIG. 5 further illustrates an automatic powered sensor applicator unit (A) in a food facility, restaurant or similar facility. Unlike the other exemplary applicators, the one shown in FIG. 5 is most suitable for rapid deployment of sensors at a large scale. Therefore, it will be appreciated a plurality of automatic applicator units can be deployed in suitable locations throughout the facility. In the illustrated embodiment, the applicator (A) is positioned above conveyors or like systems that move food underneath or nearby the applicator (A). Alternatively, the applicator (A) can be placed on a moveable system that can be positioned by food for sensor deployment and repositioned by other food for subsequent sensor deployment. It can be appreciated that modifications to the positioning of the sensor applicator unit can be made in ways that are most suitable for rapid and scalable deployment of sensors to food. In one example, the automated applicator (A) and other major components of the system (SYS) can be associated with one or more conveyor systems for tagging hosts with the monitor/detector component (B) and associated removeable/replaceable unit (C).

It will be appreciated that a wide variety of modifications can be made including those necessary for minimizing contamination and complying with other mandatory standards associated with food. For example, rapid deployment of sensors, may mean that the same removeable/replaceable injection needle assembly (00) will be used to embed sensors in multiple hosts. Therefore, sterilization of the needle may be necessary. In such case, a sterilizing solution or a material with a sterilizing solution can be used to cleanse the needle assembly after every use. Other methods include self-sterilizing polymers or other types of coatings that serve to diffuse or create a barrier to bacteria, contamination, pathogens and other harmful agents. Methods of curing and rinsing can also be used.

In some embodiments such as illustrated in FIG. 5, it can be advantageous to use automatic initiators of the injection process (03). Such mechanisms, devices or components can be initiated by motion, light, timing or an image among other optical and general features that can be programmed into software and stored in memory (12) of the automatic applicator (A).

Adaptations of the other major components can be related to methods and processes for embedding the monitor/detector (05). For example, an automated process may allow for the monitor/detector component (B) and the removeable/replaceable unit (C) to be deployed as a single unit. In some cases, the removeable/replaceable unit (C) may still be removeable, in other cases it may not be able to be removed, replaced or reused. Other adaptations may include printed elements or printed devices or printed components of at least one of such: the monitor/detector (05), connector assembly (08), power source (10), processor (11), memory (12) or communication circuitry (13). Methods can include screen printing or ink-jet printing as disclosed in U.S. Pat. No. 8,629,770 among other common methods for precision printing electronic and power components.

Other modifications to the automated sensor applicator unit (A) can be related to data processing and transmission components such as the processor (11) and memory (12). The two components are operatively coupled to the active/passive power source (10) and communication circuitry (13) for supplying power thereto, and data transmission in response to factors that can be considered triggers for initiating the sensor injection process.

The exemplary sensor applicator unit (A) embodiments illustrated in FIGS. 3-5 have been described with reference to the preferred embodiments. Obviously, modifications and alterations will occur to others upon reading and understanding the preceding detailed description. It is intended that the exemplary embodiments be construed as including all such modifications and alterations insofar as they come within the scope of the appended claims or the equivalents thereof.

Turning to FIGS. 6A-7B, various exemplary monitor(s)/detector(s) (05) are illustrated, specifically single-electrode sensors and three-electrode sensors. It will be appreciated that a monitor/detector (05) in the present disclosure is not limited to any particular sensor or detector configuration, and that aspects of the disclosure can be embodied in a wide variety of detectors. For example, a monitor/detector (05) can consist of any number of electrodes or a plurality of detectors (06) as references in FIGS. 1 and 2. Such detectors are capable of measuring or monitoring chemicals, analytes or other factors in food such as pH, temperature, humidity, moisture and nutrient availability among other relevant components such as location or journey mapping.

FIGS. 6A and 6B illustrate exemplary monitors/detectors (05) that are to be inserted into a host or can be attached to host. FIG. 6A shows an exemplary three-electrode sensor and FIG. 6B shows a single-electrode sensor. The electrodes can consist of wire, cable or other common material used for electrodes such as polymer or conductive polymer. The exemplary detectors have three major components among other adaptations aimed on improving sensor performance. The base of the sensor (17) can be an acrylic or like material coated with silver-loaded epoxy. The base of the sensor (17) can also be made entirely of silver loaded epoxy among other materials suitable for maintaining electrical conductivity between the monitor/detector (05) and the connector assembly (08).

The size, shape among other characteristics of the sensor base (17) are such that the base of the sensor (17) securely joins with the sensor electrode (18) and does not disrupt the functionality and performance of the electrode coating (19). Other considerations that affect characteristics of the sensor base (17) include the base's ability to join with the connector assembly (08) and maintain electrical connection between the monitor/detector (05) and other necessary components of the monitor/detector component (B) and the removeable/replaceable unit (C). Such necessary components can include at least one of the measurement/analyzer (09), active/passive power source (10), processor (11), memory (12) and communication circuitry (13). Methods of sensor injection shall also be considered when determining the characteristics of the sensor base (17). For example, because the monitor/detector (05) is embedded in a host using the removeable/replaceable injection assembly (00) among other applicator components, the sensor size and shape must be suitable. Other considerations include the removeable/replaceable needle assembly puncturing and passing through the sensor base, which may require a soft and moldable material that can expand or find initial shape after puncture from the needle assembly. While one of the purposes of the sensor base is to separate the electrode between the side that touches the host and the side that connects with the connector assembly and electronic components, it may also be the case that a sensor base (17) is not require. Furthermore, it may even be advantageous to not have a sensor base (17).

It will be appreciated that modifications and alterations can be made to the exemplary monitor/detector (05). Such modifications and alterations will be primarily focused on improving the accuracy and longevity of the sensor, specifically the sensor's sensitivity, selectivity, stability and response time. Other focus areas can be improving and simplifying the sensor injection process.

The sensor injection process can begin with assembling the monitor/detector (05) into a clip device (16) or like device then inserted into a removeable/replaceable sensor cartridge (02). The monitor/detector (05) can also be inserted directly into the applicator unit (A) or the clip device of sensors (16) can be inserted directly into the applicator unit (A). Next the monitor/detector (05) aligns with the injection mechanism/device/component (01) and begins the process of moving through the injection mechanism into the removeable/replaceable injection needle assembly (00). The initiator of the injection process (03) allows the needle assembly (00) to move towards the host for injection. Once the needle assembly is embedded in the host, the assembly begins to deposit the monitor/detector (05) into the host, leaving the base of the sensor (17) exposed so it can join with the connector assembly (08). Typically, the monitor/detector (05) is embedded through or on top of the connector assembly (08), which can be attached to the housing/mounting unit/connector component (07). However, alternative methods can be embraced, including embedding the monitor/detector (05) in the host first then attaching the housing/mounting unit/connector component second by way of the connector assembly (08). Next, the removeable/replaceable unit (C) is attached to the housing/mounting unit/connector component (07) by way of the connector assembly (08). Once all the components of the monitor/detector component (B) and the removeable/replaceable unit (C) are joined the system (SYS) can be calibrated and begin functioning.

Figures 7A, 7B:
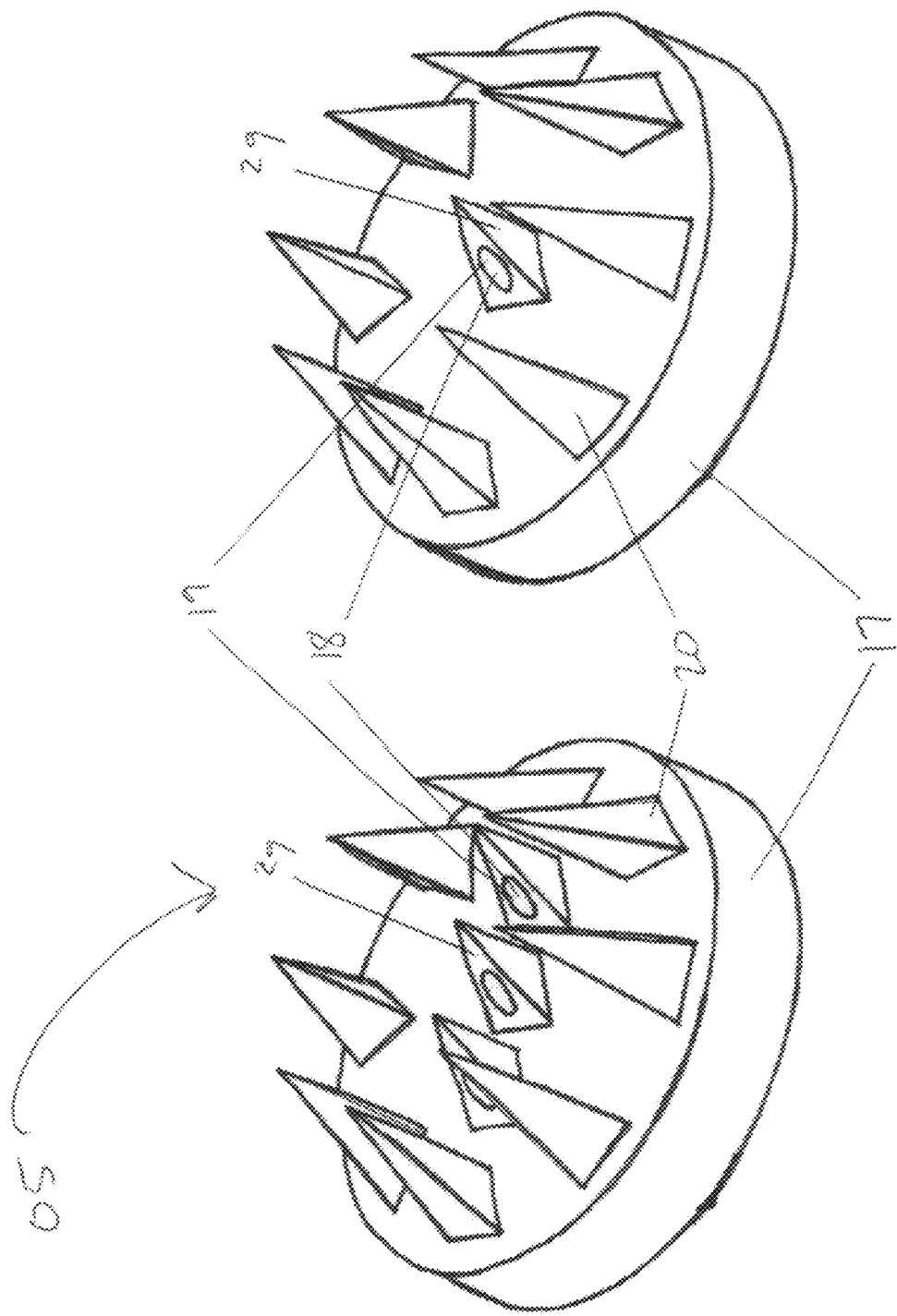
FIG. 7A is a perspective view of an exemplary sensor that can be embedded in a host or attached to a host.
FIG. 7B is a perspective view of an exemplary sensor that can be embedded in a host or attached to a host.

FIGS. 7A and 7B illustrate exemplary monitors/detectors (05) that are to be inserted into a host or placed on top of a host. FIG. 7A presents a three-electrode transdermal sensor and FIG. 7B presents a single-electrode transdermal sensor. The exemplary transdermal detectors in FIGS. 7A and 7B have similar features to those disclosed in FIGS. 6A and 6B and also have additional features. Similar features include sensor base (17), sensor electrode (18) and coating (19). The distinctions shown in FIGS. 7A and 7B include the monitor/detector (05) in the form of a microneedle or transdermal sensor rather than a wire transcutaneous electrode as shown in FIGS. 6A and 6B. Other additional features illustrated in FIGS. 7A and 7B include barbs (20) or sharp projections that allow the monitor/detector (05) to remain firmly secure or attached or embedded in a host or placed on top of host. The barbs (20) can protrude from the base of the sensor (17) and surround the sensors. Alternatively, there can be any number of barbs in any shape or any form or location as long as the barb helps to secure the sensor in place. Yet another method is to make the sensors themselves in the form of a barb or a cone-like or spike-like shape in order minimize sensor movement. The monitor/detector (05) can include one or both types of disclosed features, alternatively the monitor/detector could have neither and rely on other methods of adhesion.

The barbs (20) fulfill an especially important duty in that movement of the sensor and can significantly affect performance, especially when the sensor is in the form of a microneedle or not securely embedded in a host or attached to a host. Such microneedles can be invasive, minimally invasive or non-invasive. It will be appreciated that other methods and modifications of securing a sensor in place can be used. Alternative methods can include adhesives, pins, tags, bands, magnets among other common methods of adhesion.

Figure 8A:
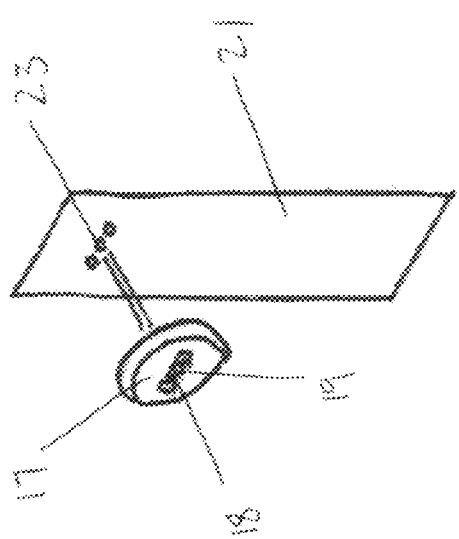
FIG. 8A is a perspective view of an exemplary connector assembly for connecting three-electrode sensors with at least one of a housing/mounting unit/connector component or a removable/replaceable unit.
Figure 8B:
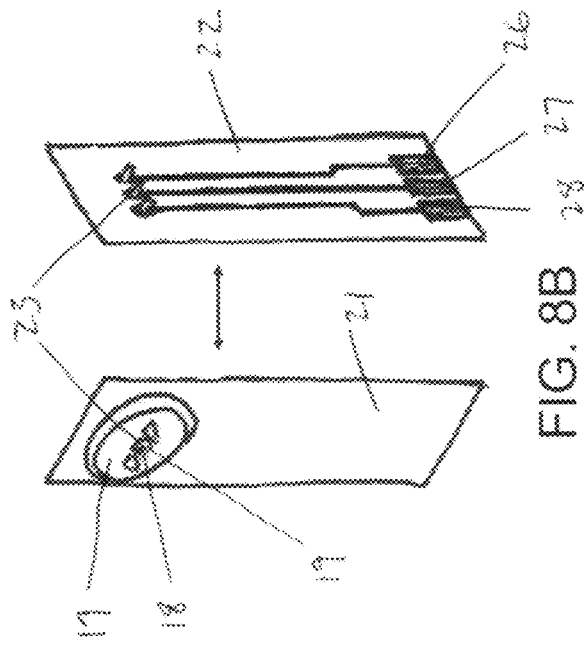
FIG. 8B is a perspective view of an exemplary connector assembly for connecting three-electrode sensors with at least one of a housing/mounting unit/connector component or a removable/replaceable unit.
Figure 8C:
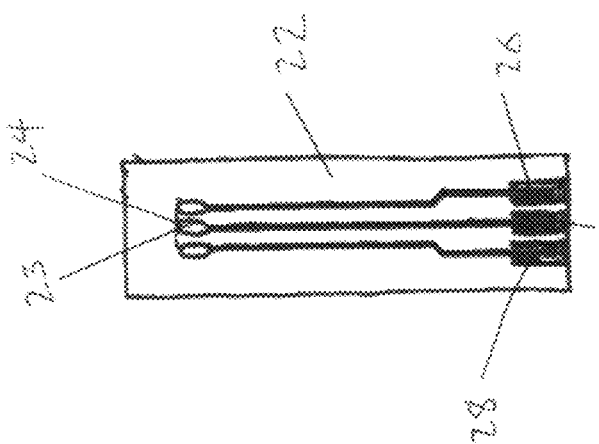
FIG. 8C is a plan view of an exemplary connector assembly for connecting three-electrode sensors with at least one of a housing/mounting unit/connector component or a removable/replaceable unit.

FIGS. 8A-8C illustrate how an exemplary connector assembly (08) join with a monitor/detector (05). The exemplary illustration shows a three-electrode sensor, however it will be appreciated that any number electrode sensor can be used as well as other types of detectors. In general, the purpose of the illustration is to show how a secure electrical connection between the monitor/detector (05) and the connector assembly (08) can be established for the purpose of furthering the electrical connection with components of the removeable/replaceable unit (C), notably the active/passive power source (10), and the measurement/analyzer (09).

Similar to FIGS. 7A and 7B, it can be appreciated that modifications and alterations can be made to the exemplary monitor/detector (05). Such modifications and alterations will be primarily focused on improving the accuracy and longevity of the sensor, specifically the sensor's sensitivity, selectivity, stability and response time. Other focus areas can be improving and simplifying the sensor injection process. One notable modification is not including a sensor base (17) on the detector itself, but rather have the sensor base (17) be part of the connector assembly (08). As previously disclosed, it may be advantageous to not include a sensor base (17) in some cases. However, the sensor base (17) helps to separate and protect the portion of the electrode wire (18) attached to the connector assembly (08), which then attaches to components of the removeable/replaceable unit (C).

FIG. 8A presents an exemplary method of joining the monitor/detector (05) with a substrate (21) or base layer of the connector assembly (08). The electrode wires (18) run through the sensor base (17) extending on both sides of the sensor base (17). On one side of the sensor base (17), the electrode wires (18) are embedded in a host or are touching a host and on the other side of the sensor base (17), the electrode wires (18) enter through the electrode connector holes (23). In the electrode connector holes (23) the electrode wires (18) are secured using silver-loaded epoxy or other forms of conductive adhesives.

Turning to FIG. 8B, an exemplary method of joining the substrate (21) with a printed electronic element (22) is shown. The printed electronic element (22) or printed electrodes can be produced using any type of precision printing or additive manufacturing method, notably metallic ink-jet and silk-screen. FIG. 8B shows a three-electrode setup including a reference electrode (RE), working electrode (WE) and counter electrode (CE).

FIG. 8C illustrates an exemplary connector assembly and the location of the conductive adhesive (24). The adhesive or silver-loaded epoxy (24) fills the electrode connector holes (23) ensuring that the electrode wires (18) are securely through the electrode connector holes (23) and joined with the printed electronic element (22), which connects to components of the removeable/replaceable unit (C). As previously disclosed, the sensor base (17) itself can be made of a conductive adhesive (24). The adhesive (24) can expand, mold or conform to securely fit with the electrode connector holes (23) and make a secure connection between the electrode wire (18) and the electronic printed element (22). Furthermore, the connection between the electrode wire (18) and the connector holes (23) and the electronic printed element (22) is critical because it allows transmission of power and data to flow from a monitor/detector (05) to components of the removeable/replaceable unit (C), primarily the measurement/analyzer (09) and the active/passive power source (10).

Figure 9A:
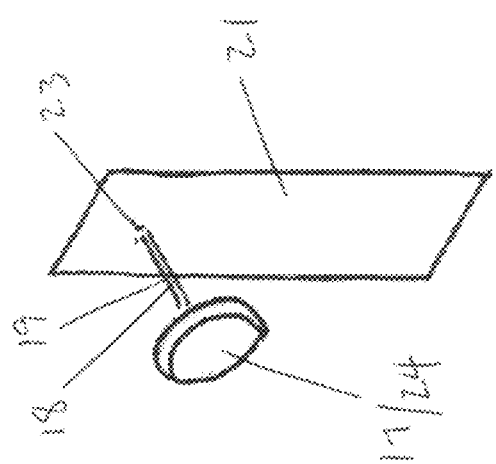
FIG. 9A is a perspective view of an exemplary connector assembly for connecting single electrode sensors with at least one of a housing/mounting unit/connector component or a removable/replaceable unit.
Figure 9B:
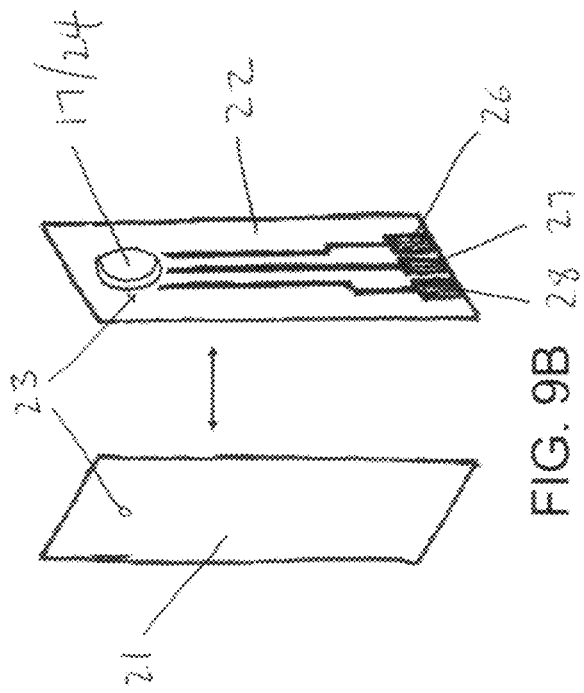
FIG. 9B is a perspective view of an exemplary connector assembly for connecting single-electrode sensors with at least one of a housing/mounting unit/connector component or a removable/replaceable unit.
Figure 9C:
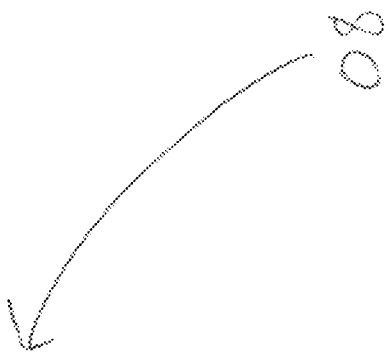
FIG. 9C is a plan view of an exemplary connector assembly for connecting single-electrode sensors with at least one of a housing/mounting unit/connector component or a removable/replaceable unit.

FIGS. 9A-9C present a similar exemplary method for joining a monitor/detector (05) to a connector assembly (08) as shown in FIGS. 8A-8C. However, the exemplary method illustrated in FIGS. 9A-9C relate to a single-electrode sensor. FIG. 9A illustrates the monitor/detector (05) joining with the substrate (21) and the sensor base (17) conforming to the electrode connector hole (23). FIG. 9B illustrates how the printed electronic element (22) goes on top of the substrate (21) with the sensor base (17) filling and conforming to the electrode connector hole (23) so that a secure connection is established between the electrode wire (18) and the printed electronic element (22). As previously disclosed, the sensor base (17) can be of a conductive adhesive (24) or other adhesive can be added in order to establish a secure connection between the electrode wire (18) and the printed electronic element (22). FIG. 9C illustrates the printed electronic element (22) on top of the substrate (21)

with the electrode connector hole (23) filled with a conductive adhesive (24), which can be in the form of an epoxy or sensor base (17).

FIGS. 10A-10D are schematic views that illustrate portions of the removeable/replaceable injection assembly (00), injection mechanism/device/component (01), monitor detector (05), connector assembly (08) as well as supporting components at various stages of the insertion of subcutaneous sensor. FIG. 10A illustrates the removeable/replaceable needle assembly (00) loaded with the electrode wire (18) and injection mechanism/device/component (01) prior to insertion into host and after insertion into the electrode connector hole (23) of the connector assembly (08). FIG. 10B illustrates the needle assembly (00) loaded with the electrode wire (18) and the injection mechanism/device/component (01) after insertion into the electrode connector hole (23) of the connector assembly (08) and after insertion into host. FIG. 10C illustrates the needle assembly (00) releasing the electrode wire (18) into the host as the needle assembly (00) retracts through the electrode connector hole (23) of the connector assembly (08). FIG. 10D illustrates the needle assembly (00) free from the electrode wire (18) and fully retracted from the host and the electrode connector hole (23) of the connector assembly (08). FIG. 10D also shows the electrode wire (18) successfully deposited in the host and conductive adhesive (24) or sensor base (17) securing an electrical connection between the electrode wire (18) and the printed electronic element (22) through the electrode connector hole (23). It also shows the sensor base (17) in the form of an expandable, moldable conductive adhesive (24) enabling the secure connection. Additional adhesive (24) is also shown to help establish a secure electrical connection between the electrode wire (18) and the printed electronic element (22). It may also be the case that a barb (20) or like component is part of the end of the electrode wire (18) closer to the sensor base (17), which allows the electrode wire to remain securely embedded in a host.

Furthermore, FIGS. 10A-10D present an exemplary method of how the removeable/replaceable injection needle assembly (00) and the injection mechanism/device/component functions to embed the electrode wire (18) in a host. The assembly (00) helps facilitate sensor insertion and subsequent needle retraction. The assembly (00) can include a needle carrier and a needle. The needle carrier cooperates with the other applicator components and carries the needle between its extended and retracted positions. The needle can be of any appropriate size that can encompass the sensor and aid in its insertion into the host. The needle carrier is configured to engage with a guide tube carrier, while the needle is configured to slidably nest within the guide tube, which allows for easy guided insertion (and retraction) of the needle through the contact subassembly.

Figure 11A:
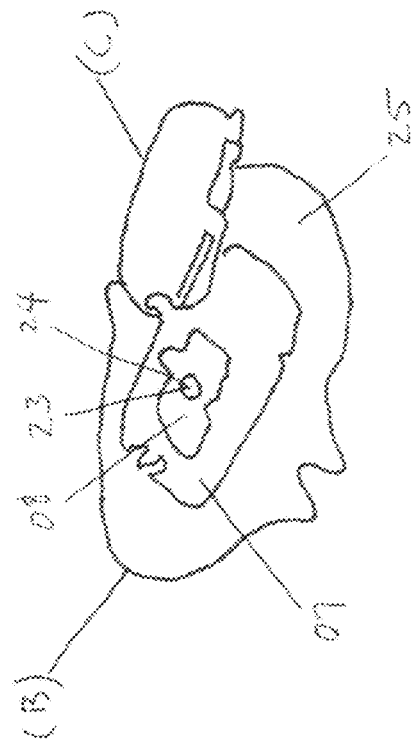
FIG. 11A is a side view of an exemplary sensor monitoring device for a single-electrode sensor.
Figure 11C:
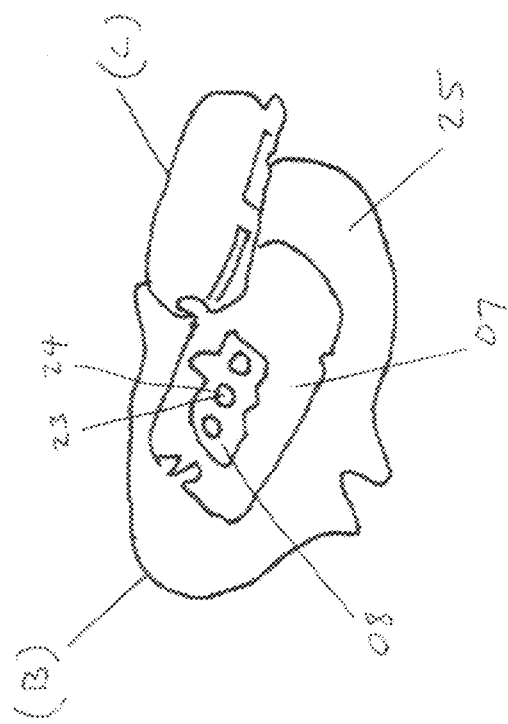
FIG. 11C is a side view of an exemplary housing/monitoring unit/connector component for a single-electrode sensor.
Figure 11B:
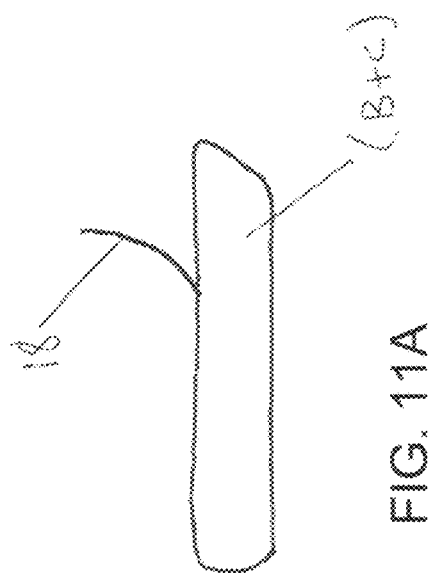
FIG. 11B is a side view of an exemplary sensor monitoring device for a three-electrode sensor.

FIGS. 11A-11D present exemplary configurations of two of the major system components—the monitor/detector component (B) and the removeable/replaceable unit (C), otherwise known as (B+C) or the monitoring device. The FIGS. 11A-11C illustrate both a single-electrode setup as well as a three-electrode setup. FIG. 11A shows a monitor/detector (05) in the form of a single electrode wire (18) protruding from the combined unit of the monitor/detector component (B) and the removeable/replaceable unit (C). FIG. 11B is similar to 11A, however the only difference is that FIG. 11B shows three monitor/detectors (05) in the form an electrode wires (18) protruding from the combined unit of the monitor/detector component (B) and the removeable/replaceable unit (C).

Figure 11D:
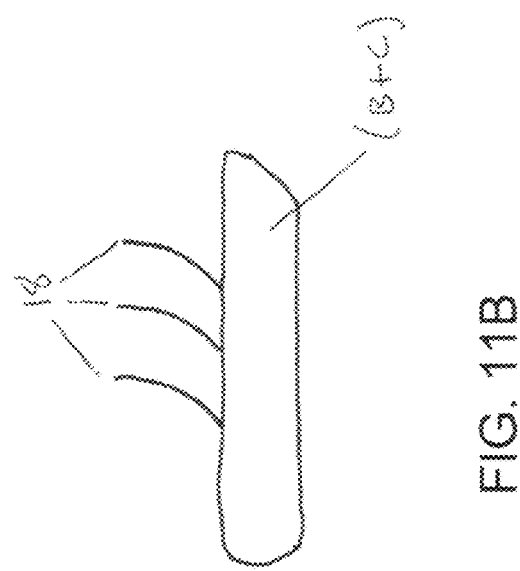
FIG. 11D is a side view of an exemplary housing/monitoring unit/connector component for a three-electrode sensor.

FIG. 11C illustrates an exemplary configuration of the monitor/detector component (B) and the removeable/replaceable unit (C), specifically how the two units are capable of attaching and detaching or selectively attach. The removeable/replaceable unit (C) fastens to the housing/mounting unit/connector component (07), which is joined to the connector assembly (08). The electrode connector hole (23) of the connector assembly (08) is shown. As previously disclosed, the removeable/replaceable injection needle assembly loaded with the wire electrode (18) penetrates the conductive adhesive (24) covering the electrode connector hole (23) as it deposits the wire electrode (18) into the host. With most of the electrode inside of the host, the remaining portion extends through the electrode connector hole (23) making a secure connection between the portion of the wire electrode (18) not inside the host and printed electronic element (22) of the connector assembly (08) through the electrode connector hole (23). FIG. 11C also illustrates an adhesive pad (25) or like substance that allows the housing/mounting unit/connector component (07) to stay attached to the host. FIG. 11D is similar to 11C, however the only difference is that FIG. 11D shows a set-up for a three-electrode sensor instead of the single-electrode sensor setup shown in FIG. 11C.

Figure 12B:
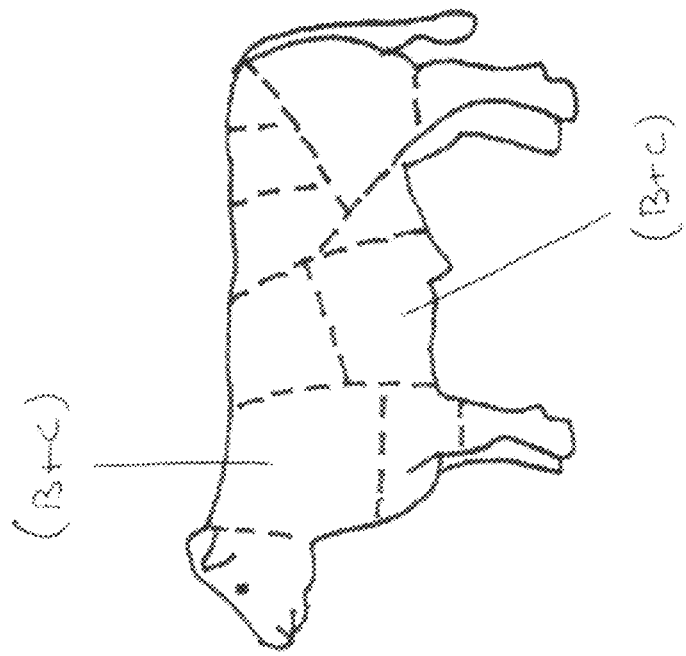
FIG. 12B illustrates exemplary locations of sensor monitoring devices to be attached or embedded in meat food product.
Figure 12A:
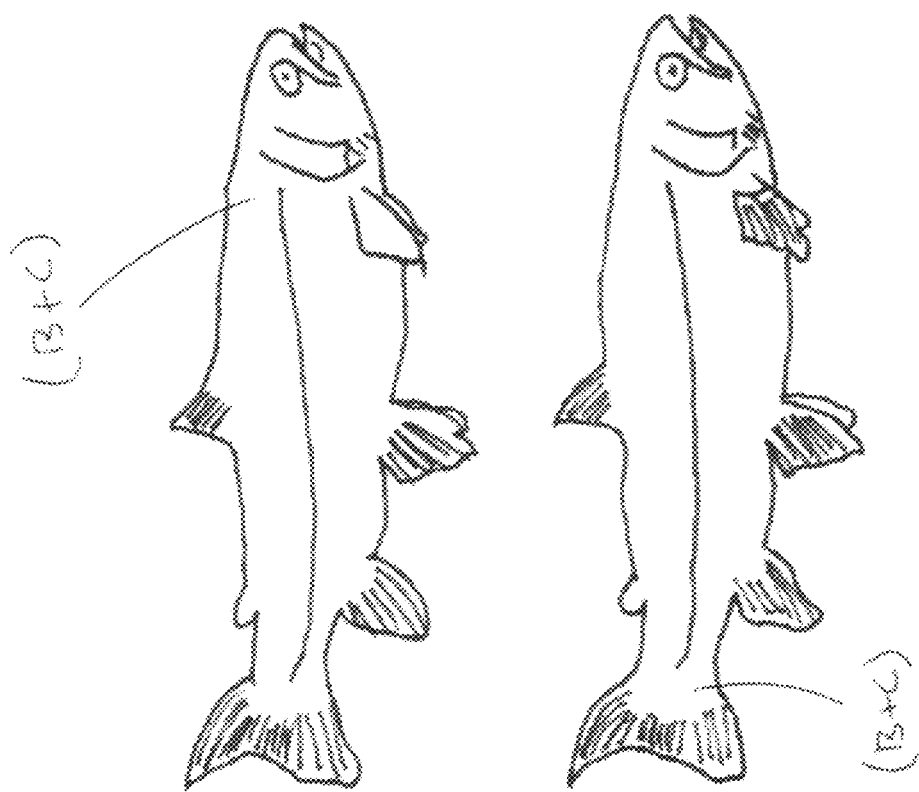
FIG. 12A illustrates exemplary locations of sensor monitoring devices to be attached or embedded in fish food product.

FIGS. 12A-12B present exemplary hosts as well as locations on the hosts where the combined monitor/detector component (B) and removeable/replaceable unit (C) known as (B+C) or the monitoring device can be located. While monitoring devices intended to be attached to a host, it can also be attached to pieces or segments of a host. For example, a host such as a fish or a cow are routinely cut into pieces. The sensors can be attached to not only the whole fish or whole cattle, but also pieces of the fish or cattle. FIG. 12A shows exemplary locations for the monitoring device on a host in the form of a fish. It can be appreciated that the location of the monitoring device considers several factors including sensor performance and threat of contamination among other factors related to operability. For example, (B+C) or the monitoring device can be placed in a location on the host where it is most likely to stay securely attached, limiting sensor interference. The location of the monitoring device shall also consider where spoilage and contamination are likely to occur early and often. The location of (B+C) or the monitoring device may also be in a part of host not likely to be consumed by humans so to avoid contamination from the device. Also, the location of the monitoring device shall be selected based on considerations related to processing, packaging and transporting the host among other considerations unique to a food retailer. Among the possible locations of (B+C) or the monitoring device on a fish include the top portion between the head and top fin area, being closer to the head. Another possible location of the monitoring device is in a meaty portion of the tail. Yet another location includes the head area closer to the gills.

FIG. 12B illustrates the many types of cuts of beef as exemplary locations for (B+C) or the monitoring device. The steps of meat processing are well known, among them include cutting cattle into portions that resemble end products. FIG. 12B shows the various portions including chuck, brisket, shank, rib, plate, flank, loin, rump, round and hind shank. Each of these cuts can be processed, boxed and packaged individually or collectively. For example, often times cattle are cut into large pieces resembling their end products and shipped to stores or facilities for further processing. The sensor monitoring device (B+C) can be attached to large chunks of meat transported and stored in boxes or other suitable containers. Stated more simply, (B+C) or the sensor monitoring device can be attached or embedded to any and all of the portions of seafood, meat or other perishable foods. The sensor devices can be placed on portions of meat or fish, removed for processing, then re-placed on smaller portions or cuts from the initial portions.

Figure 13B:
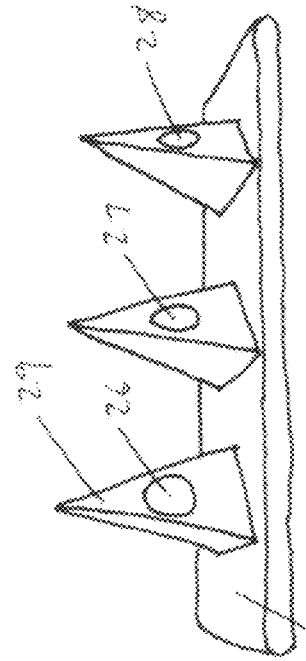
FIG. 13B is a perspective view of a single three-electrode microneedle sensor.
Figure 13D:
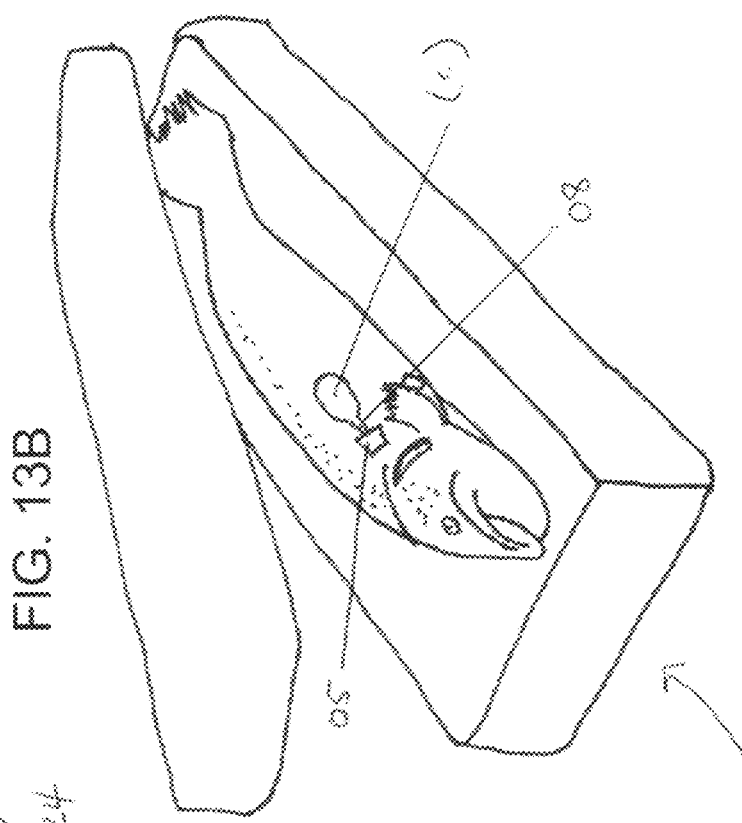
FIG. 13D is a perspective view of a monitoring device (B+C) attached to a fish that is stored and transported in an EPS box; and, FIG. 14 presents experimental sensor data measuring concentrations of chemicals associated with spoilage and contamination.
Figure 13A:
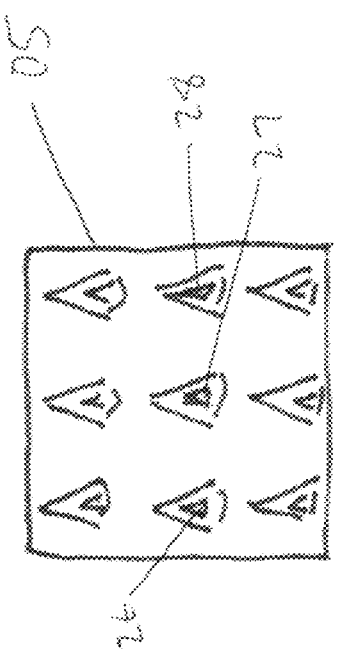
FIG. 13A is a plan view of a transdermal microneedle sensor array for detecting multiple chemicals or analytes in a host or food product.
Figure 13C:
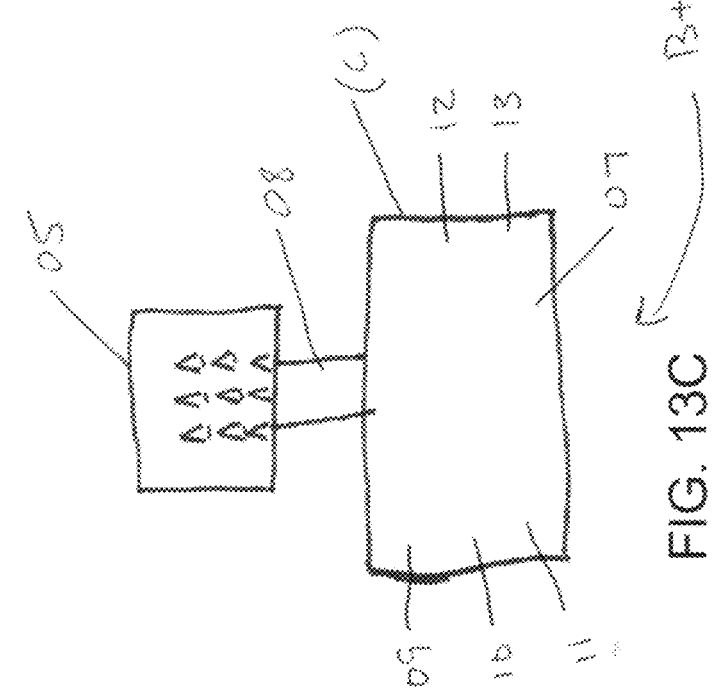
FIG. 13C is a schematic illustration of an exemplary sensor monitoring device (B+C)

FIGS. 13A-13D present yet another exemplary configuration of the sensor monitoring device (B+C) and how it can be deployed to measure, and monitor chemicals and analytes associated with spoilage and contamination of a fish transported and stored in an expanded polystyrene foam (EPS) box. FIG. 13A presents an exemplary monitor/detector (05) in the form of a transdermal microneedle sensor array for detecting multiple chemicals or analytes in a host or food. FIG. 13B presents a schematic representation of a single three-electrode microneedle sensor, however it can be appreciated that any number of electrode sensor can be used. FIG. 13C presents an exemplary sensor monitoring device (B+C). The monitor/detector component (B) is selectively attachable to the removeable/replaceable unit (C), that contains a micro-board and various sub-components such as measurement/analyzer (09), active/passive power source (10), processor (11), memory (12) and communication circuitry (13) as well as housing (07).

FIG. 13A shows a monitor/detector (05) in the form of a transdermal microneedle electrode sensor. The microneedle can be of a hollow enzyme biosensor. One such configuration can rely on the coupling of the effective biocatalytic action of a chemical with a hollow microneedle modified carbon-paste array electrode transducer, involving rapid square-wave voltammetric (SWV) measurements of an analyte or byproduct of the enzymatic reaction in the presence of a substrate for a target chemical. The scanning-potential SWV transduction mode offers an additional dimension of selectivity compared to common fixed-potential.

FIG. 13B present a closer schematic representation of a single three-electrode transdermal microneedle sensor. The monitor/detector (05) consists of three electrodes including a counter electrode (26), working electrode (27) and reference electrode (28). The reference electrode is typically in the form of a silver chloride or Ag/AgCl electrode. In this particular design, the electrodes are enclosed in a cone (29) made of a biocompatible polymer or conductive polymer or self-sterilizing polymer. The cones extend from the base of the sensor (17), which can also be made of biocompatible material including silver-loaded epoxy. However, it may also be the case that many materials can be polymerized into desired component geometries created using computer aided design software. It may also be the case that non-biocompatible materials may be made biocompatible. After the sensor base (17) and cones (29) are fabricated using a precision or 3D printing process or additive manufacturing, comes a microtereolithography step. Typically, the sensors are rinsed with isopropanol several times and dried. Other steps include soaking in isopropanol and sonicated in ultrasonic bath. The purpose of this step is to remove any unpolymerized resin. It can be appreciated that other means of doing so can be incorporated in these disclosed processes. Before, undergoing a post curing procedure, the sensors are dried in a heater chamber at 30 degrees Celsius for at least 30 minutes. For post curing, the sensors are loaded into an Otoflash Post Curing Light Pulsing Unit and exposed to two sets of 2000 light pulses. Light pulses in the 300-700 nm spectral range are utilized at 10 Hz to polymerize residual unpolymerized material within the devices. The devices are then imaged to ensure they are free from printing flaws.

FIG. 13C presents an exemplary configuration of the sensor monitoring device (B+C). The monitor/detector (05) in the form of a microneedle array is connected to the removeable/replaceable unit (C) through the connector assembly (08). The microneedle array could be made with barbs or other suitable mechanisms such as bands, pins or adhesives that allow the microneedle to be securely attached to a host or food (see FIG. 7A-7B). The removeable/replaceable unit (C) contains a measurement/analyzer (09), active/passive power source (10), processor (11), memory (12) and communication circuitry (13). The sensor monitoring device (B+C) can also have a housing (07) that protects the components. The housing (07) can cover or house components of the removeable/replaceable unit (C) or the housing (07) can cover or house also components of the monitor/detector component (B). In other designs, the monitoring device (B+C) may be of printed elements or components and not require a housing (07).

FIG. 13D presents an exemplary application of the sensor monitoring device (B+C). The monitoring device (B+C) is attached to a fish that is stored and transported in an EPS box. As previously disclosed in FIG. 12, the location of the monitoring device depends on various considerations. FIG. 13D show the monitoring device (B+C) attached to the side of the fish lying up facing the top of the EPS box. It can be appreciated that various configurations of the monitoring device (B+C) can be embedded or attached to various food items transported and stored in boxes, containers, bags, crates, bins among other food storage and transportation equipment. It can also be appreciated that the device will be sterilized in order to avoid contamination and other harmful factors.

Figure 14:
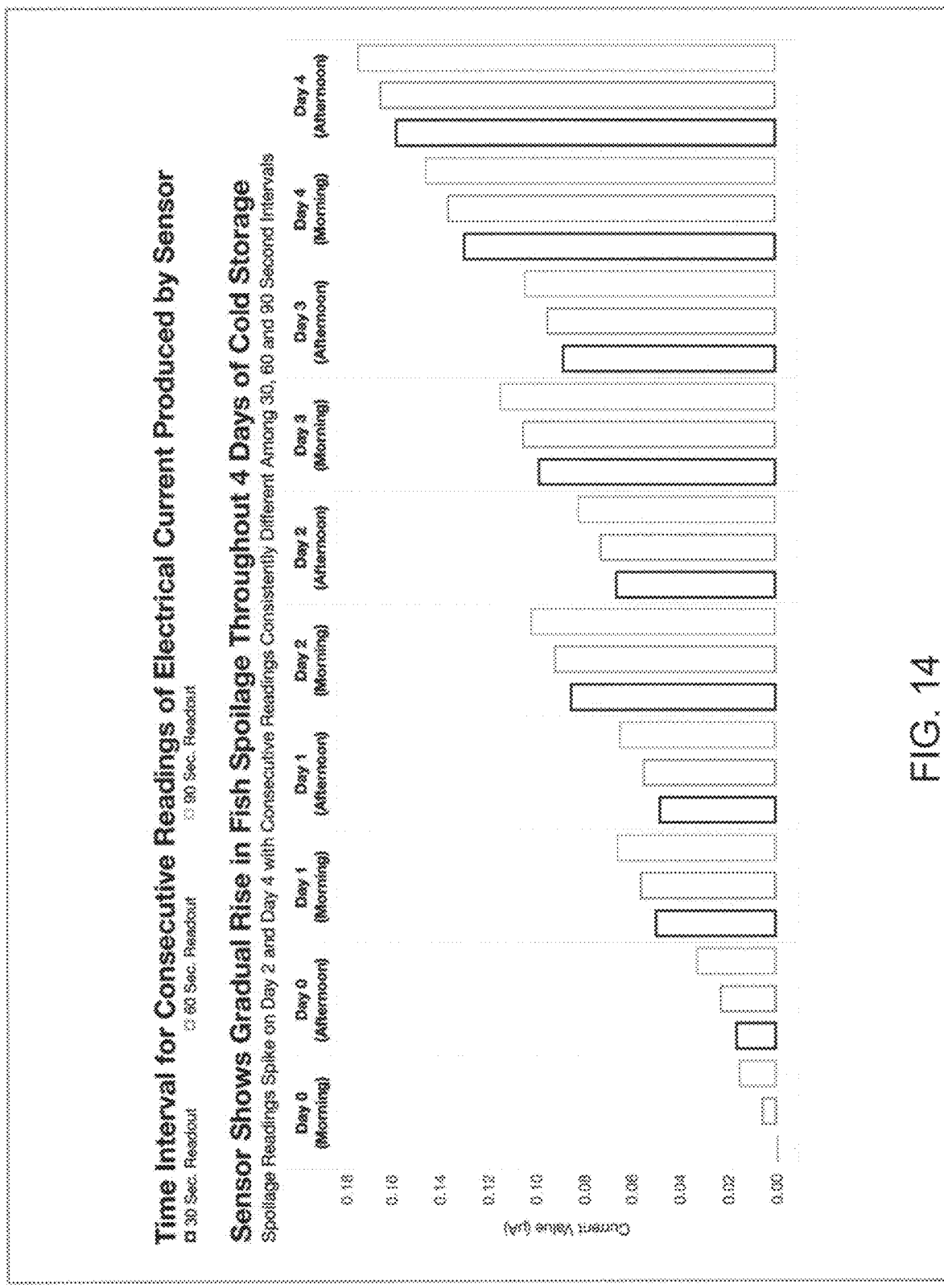

FIG. 14 presents experimental sensor data measuring concentration levels of hypoxanthine in a fresh salmon over a 4-day period. The salmon was stored in an EPS box under cold chain conditions ranging between 0 and 4 Celcius. The chart shows concentration levels of hypoxanthine rising over time with spikes on day 2 and day 4 of storage. The spoilage values were calculated based off of hundreds of readings within each time interval category—30 seconds, 60 seconds and 90 seconds. These categories are defined by the time that is required to gather sensor data. For example, the 90 second intervals have 3 times as much data as the 30 second intervals and 2 times as much data as the 60 second intervals. The chart shows the difference in intervals to be consistent for each spoilage value allowing the use the 30 second interval, which requires less power, for a highly accurate spoilage measurement (i.e. concentration levels of hypoxanthine).

The exemplary embodiments have been described with reference to the preferred embodiments. Obviously, modifications and alterations will occur to others upon reading and understanding the preceding detailed description. It is intended that the exemplary embodiment be construed as including all such modifications and alterations insofar as they come within the scope of the appended claims or the equivalents thereof.

The invention claimed is:

1. A device for measuring one or more analytes in a food product, the device comprising:
   at least one detector component operative to generate data in response to detection of one or more analytes in the food product and use the data to predict nutrient, spoilage and/or contamination levels in the food product; wherein said device determines at least one of a location or operating status of the at least one detector component;

communication circuitry; and
a power source comprising an antenna for receiving energy wirelessly and operatively coupled to the at least one detector component and the communication circuitry for supplying received energy thereto;
wherein the communication circuitry is configured to transmit data generated by the at least one detector component corresponding to the presence or absence of a concentration level of the one or more analytes to an associated receiver; and wherein an algorithm is used to use data from the at least one detector to predict the time the food product will be in a food supply chain without spoiling;
wherein the at least one detector component includes:
a detector;
a connector assembly having a printed electronic element; and
a mounting unit for the connector assembly;
wherein at least one of the at least one detector component, communication circuitry or power source is part of a unit which is removable or replaceable that attaches to the connector assembly and mount;
wherein the detector has one or more conductive surfaces at a first end of the detector and one or more connection surfaces at a second end of the detector;
wherein the one or more conductive surfaces are configured to engage a surface of the food product or embed in the food product using one or more barbs which protrude from a base of the sensor and remain in or on the food product and are configured to secure the sensor in place with the food product;
wherein the one or more connection surfaces are configured to operably connect to the connector assembly, establishing electrical contact between the detector and power source and communication circuitry; and
wherein the detector is operatively coupled to the power source and communication circuitry by penetrating a conductive adhesive seal of an electrode connector hole of the connector assembly whereby the at least one connection surface of the detector extend through the electrode connector hole making a secure electrical connection between the at least one connection surface of the detector and the printed electronic element of the connector assembly;
and a sensor that measures at least one of temperature, humidity, moisture, pH, location, shock or vibration.

2. The device of claim 1, wherein the unit further includes at least one of a measurement analyzer, processor or memory.

3. The device of claim 1, wherein the at least one detector includes at least one of a transcutaneous sensor, transdermal sensor, electrochemical sensor or chemiresistor or a spectroscopy sensor for measuring an analyte.

4. The device of claim 1, further comprising a housing supporting the at least one detector component, communication circuitry, and power supply, the housing includes a connector component that mates with an applicator unit for deployment of one or more detectors.

5. The device of claim 4, wherein at least one of the detector, housing, mounting unit, connector component, connector assembly, power source, memory, processor, communication circuitry or measurement analyzer includes a printed element or component.

6. The device of claim 1, further comprising an adhesive pad for securing the device to the food product.

7. A system for measuring an analyte or other factor in a food product, the system comprising:
a receiver;
an applicator unit for embedding or applying at least one detector to the food product using one or more barbs which protrude from the sensor and keep the sensor embedded on the food product, the applicator unit comprising:
an injection device;
an injection needle assembly that is removable or replaceable; and
a housing component;
a device for measuring analytes or other factors in the food product, the device comprising:
at least one detector component operative to generate data corresponding to a presence or an absence of at least one analyte or characteristic of the food product and use the data to predict nutrient, spoilage and/or contamination levels in the food product wherein at least one detector component measures at least one of temperature, humidity, moisture, pH, location, shock or vibration;
communication; and
a power source comprising an antenna operatively coupled to the detector component and the communication circuitry for supplying power thereto;
wherein the communication circuitry is configured to transmit the data generated by the at least one detector component to the receiver; and wherein an algorithm is used to use the data from the at least one detector to predict a time the food product is in a food supply chain prior to spoiling.

8. The system of claim 7, further comprising at least one of a measurement analyzer, processor or memory that is included in a unit that is removable or replaceable.

9. The system of claim 7, wherein the at least one detector component includes at least one of a transcutaneous sensor, transdermal sensor, electrochemical sensor, chemiresistor or spectroscopy sensor for measuring an analyte or other factor.

10. The system of claim 7, wherein at least one of the at least one detector component, housing, mounting unit, connector component, connector assembly, power source, memory, processor or communication circuitry is of a printed element or component.

11. A method of measuring analytes or other factors associated with spoilage, contamination and/or pathogens in a supply chain and storage of food products, the method comprising:
providing a plurality of sensors, each sensor including:
one or more detector components which engage a surface of the food product and are embedded in the food product operative to generate data in response to the presence or absence of one or more analytes or other factors in the food products including location, temperature, pH, moisture and humidity and use the data to predict at least one of nutrient, spoilage and/or contamination levels in the food products; said one or more detector components measures at least one of temperature, humidity, PH, shock or vibration;
communication circuitry; and
a power source comprising an antenna for receiving energy wirelessly and operatively coupled to the one or more detector components and the communication circuitry for supplying received energy thereto;
wherein the communication circuitry is configured to transmit data generated by the one or more detector components corresponding to a presence or an absence of one or more analytes or other factors including location, temperature, pH, moisture and humidity to an associated receiver;

associating each sensor with a shipment and the shipment's location, or area to be monitored and the area's location;

monitoring each shipment or location or area with its associated sensor over a period of time; and transmitting data generated by each sensor to a receiver; and using an algorithm to interpret the data and predict (a) a length of time the food product can remain in the supply chain from a producer to a store or retailer;

b) the length of time the food product can remain at the store or retailer;

and c) the length of time the food product can remain with a consumer after purchase prior to spoiling.

12. The method of claim 11, further comprising at least one of a measurement analyzer, processor or memory that is included in a unit that is removable or replaceable.

13. The method of claim 11, wherein the one or more detector components includes a transcutaneous sensor or transdermal sensor or an electrochemical sensor or chemiresistor or spectroscopy sensor for measuring an analyte.

14. The method of claim 11, wherein at least one of the detector component, housing, mounting unit, connector component, connector assembly, power source, memory, processor or communication circuitry is of a printed element or component.

* * * * *